United States Patent
Roberts et al.

(10) Patent No.: US 6,494,084 B1
(45) Date of Patent: Dec. 17, 2002

(54) ADJUSTABLE SHEAR STRESS EROSION AND TRANSPORT FLUME

(75) Inventors: Jesse D. Roberts, Carlsbad, NM (US); Richard A. Jepsen, Carlsbad, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 09/955,640

(22) Filed: Sep. 19, 2001

(51) Int. Cl.$^7$ ............................................. G01N 17/00
(52) U.S. Cl. .......................................................... 73/86
(58) Field of Search ................................... 73/86, 841

(56) References Cited

U.S. PATENT DOCUMENTS

| | | | |
|---|---|---|---|
| 5,243,850 A | 9/1993 | Hanson | 73/86 |
| 5,479,724 A | 1/1996 | Nahajski | 33/179 |
| 5,753,818 A | 5/1998 | Mercado | 73/594 |
| 6,260,409 B1 | 7/2001 | Briand | 73/86 |

OTHER PUBLICATIONS

McNeil, Taylor and Lick; Measurements of Erosion of Undisturbed Bottom Sediments with Depth; Jun. 1996; pp. 316–324.

Jepsen, McNeil and Lick; Effects of Gas Generation on the Density an Erosion of Sediments from the Grand River; pp. 209–218, 2000.

Robert, Jepsen, Gotthard & Lick; Effects of Particle Size and Bulk Density on Ersion of Quartz Particles; Dec. 1998; pp. 1261–1267.

Jepsen, Roberts and Lick; Effects of Bulk Density on Sediment Erosion Rates; 1997; pp. 21–31.

Leo C. van Rijn; Sediment Transport, Part I: Bed Load Transport; Oct. 25, 1982; pp. 1431–1467.

Roberts, Jepsen & Gailani; Measurements of Bedload and Suspended Load in Cohesive and Non–Cohesive Sediments, May 24, 2001.

*Primary Examiner*—Robert Raevis
(74) *Attorney, Agent, or Firm*—Robert D. Watson

(57) ABSTRACT

A method and apparatus for measuring the total erosion rate and downstream transport of suspended and bedload sediments using an adjustable shear stress erosion and transport (ASSET) flume with a variable-depth sediment core sample. Water is forced past a variable-depth sediment core sample in a closed channel, eroding sediments, and introducing suspended and bedload sediments into the flow stream. The core sample is continuously pushed into the flow stream, while keeping the surface level with the bottom of the channel. Eroded bedload sediments are transported downstream and then gravitationally separated from the flow stream into one or more quiescent traps. The captured bedload sediments (particles and aggregates) are weighed and compared to the total mass of sediment eroded, and also to the concentration of sediments suspended in the flow stream.

81 Claims, 16 Drawing Sheets

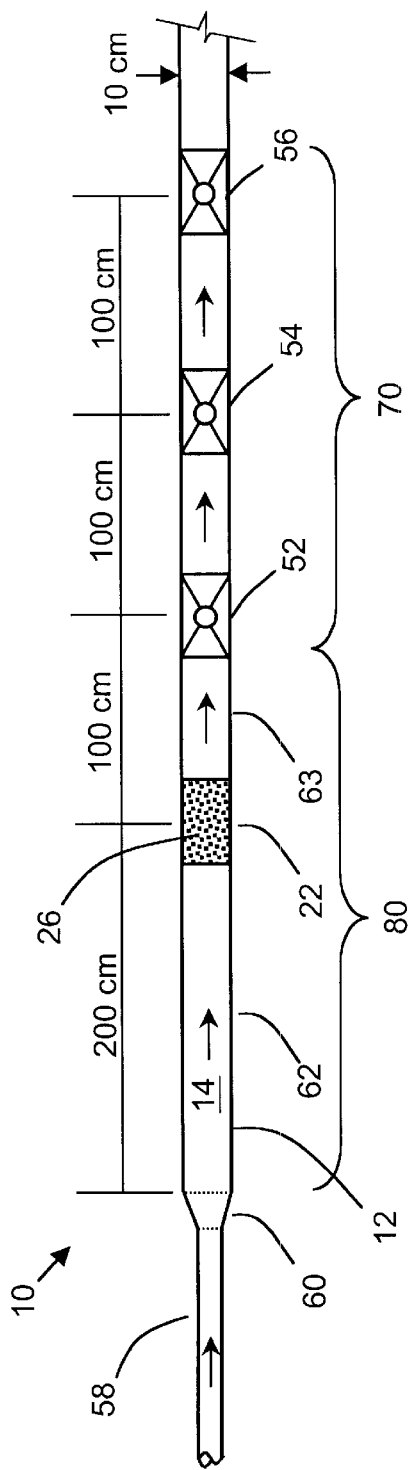
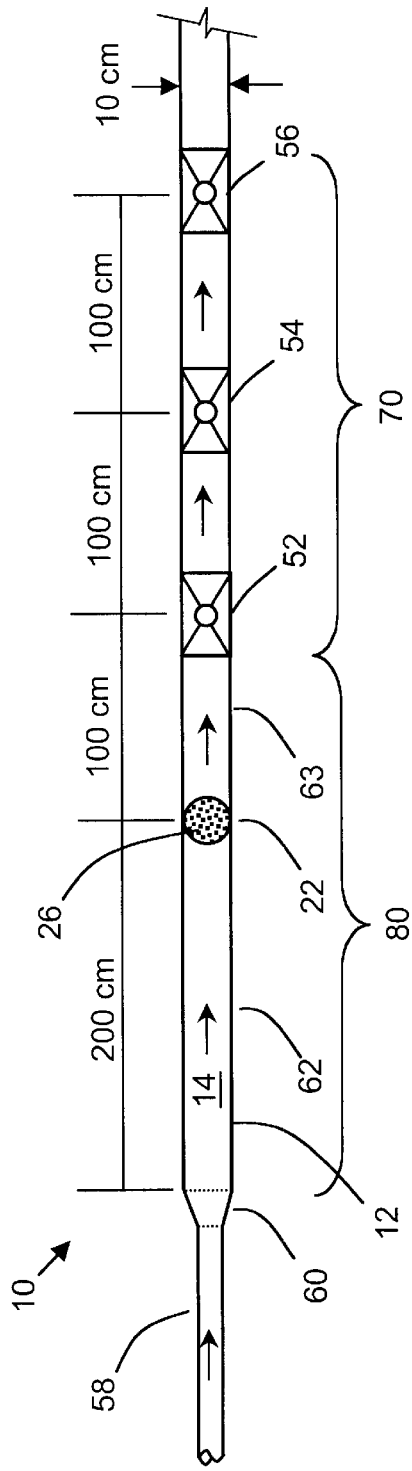
Fig. 5A
Fig. 5B

ADJUSTABLE SHEAR STRESS EROSION AND TRANSPORT FLUME

FEDERALLY SPONSORED RESEARCH

The United States Government has rights in this invention pursuant to Department of Energy Contract No. DE-AC04-94AL85000 with Sandia Corporation.

BACKGROUND OF THE INVENTION

The present invention relates generally to a method and apparatus for measuring aqueous erosion and transport from a sediment core sample and, in particular, to an adjustable shear stress erosion and transport flume having a variable depth sediment core sample.

Many contaminants are sorbed to sedimentary particles and are buried at depths of up to several meters in the bottom sediments of rivers, lakes, estuaries, and near-shore areas of the oceans. An important question is whether these buried sediments (and associated contaminants) can be exposed and transported during large floods and storms. In order to answer this question, knowledge of the erosion and transport properties of sediments at high shear stresses (up to and exceeding 10 $N/m^2$) and with depth through the sediment layer (up to and exceeding one meter) is needed.

To characterize the movement of sediments in aquatic systems one must not only have an understanding of the bulk erosion rates of sediments, but also be able to distinguish between two primary modes of sediment transport, i.e., suspended transport and bedload transport. As shown in FIG. 1, suspended transport of a sediment grain or particle in flowing water occurs when the vertical component of the turbulent flow velocity is approximately equal to or greater than the settling (i.e., falling) speed of the grain. Unsuspended transport, also known as bedload transport, includes a variety of transport mechanisms, such as saltation, rolling, sliding, and tumbling. Saltation occurs when a particle momentarily leaves the bed and rises no higher than a few grain diameters. Rolling, sliding, and tumbling are additional processes wherein particles are transported along the bed primarily by the horizontal force of the overlying flow of water. In bedload transport, the particles receive no significant upward impulses other than those due to successive contacts between the solid and the bed; the fluid impulses on the grains being essentially horizontal. Saltation transport is generally included in bedload transport since saltation is restricted to only a few grain diameters in height above the bed.

Erosion of sediments in river and streambeds, along ocean beaches, harbors, and waterways, and around bridge support structures, is a complex process that depends on many variables. Sediments may erode particle-by-particle (e.g., sand and gravel), or may erode as aggregates or chunks, especially if the particles are fine-grained and cohesive (e.g., clay or silt). The chunks can vary in size from microns to centimeters, generally do not re-suspend, and are made from very fine-grained particles that would re-suspend if disaggregated. Sediments may also be contaminated with chemical, biological, or industrial contaminants, which can affect the degree of cohesiveness. Erosion and transport rates can also depend on grain size, shape, density, degree of cohesiveness, chemistry, organic content, and gas content. As shown in FIG. 2, aggregated (cohesive) particles eroded from the bed at an upstream position, $X_1$, can de-aggregate at a downstream position, $X_2$, due to subsequent impacts and collisions with the channel bottom and/or other aggregates and particles (e.g., during saltation transport). Erosion rates and transport modes also depend on the shear stress applied across the sediment's surface by velocity of the flowing liquid (e.g., water). Typically, a threshold exists where no appreciable erosion occurs below a critical shear stress.

Accurate prediction of erosion rates (bulk or total, suspended, and bedload) and subsequent transport and re-deposition for each mode of transport (suspended or bedload) is complicated by a lack of understanding of the cohesive forces that bind together fine-grained sediments (especially for contaminated sediments). Therefore, a need exists for an apparatus and method that can accurately measure the individual contributions to the total erosion rate of sediments from suspended and bedload erosion processes, whether in the laboratory or in the field.

There is an existing apparatus for measuring bulk erosion of sediments (without transport), called a "SEDflume", which is described in "Measurements of Erosion of Undisturbed Bottom Sediments with Depth", J. McNeil, C. Taylor, and W. Lick, Journal of Hydraulic Engineering, June, 1996. A similar device is also described in U.S. Pat. No. 6,260,409 to Briaud, et al., "Apparatus and Method for Prediction of Scour Related information in Soils". However, these devices can only measure the total (i.e., bulk) erosion rate of a sediment core sample without any downstream transport, and, hence, cannot independently measure the separate contributions from suspended and bedload erosion while being transported down a channel.

Against this background, the present invention was developed.

SUMMARY OF THE INVENTION

The present invention relates to a method and apparatus for measuring the total erosion rate and downstream transport of suspended and bedload sediments using an adjustable shear stress erosion and transport (ASSET) flume with a variable-depth sediment core sample. Water is forced past a variable-depth sediment core sample in a closed channel, eroding sediments, and introducing suspended and bedload sediments into the flow stream. The core sample is continuously pushed into the flow stream, while keeping the surface level with the bottom of the channel. Eroded bedload sediments are transported downstream and then gravitationally separated from the flow stream into one or more quiescent traps. The captured bedload sediments (particles and aggregates) are weighed and compared to the total mass of sediment eroded, and also to the concentration of sediments suspended in the flow stream.

BRIEF DESCRIPTION OF THE DRAWINGS

The accompanying drawings, which are incorporated in and form part of the specification, illustrate various examples of the present invention and, together with the detailed description, serve to explain the principles of the invention.

FIG. 5A shows a schematic elevation view of an adjustable shear stress erosion and transport (ASSET) flume with multiple traps and a rectangularly-shaped sediment core sample, according to an embodiment of the present invention.

FIG. 5B shows a schematic elevation view of an adjustable shear stress erosion and transport (ASSET) flume with multiple traps and a cylindrically-shaped sediment core sample, according to an embodiment of the present invention.

DETAILED DESCRIPTION OF THE INVENTION

Herein, we define erosion to include scouring. We define the bulk or total erosion rate to equal the sum of the suspended erosion rate and the bedload erosion rate. We define sediments to include grains, particles, particulates, and aggregates (or chunks) of grains or particles that are adhered together with cohesive forces. We define bedload transport processes to include saltation, rolling, sliding, and tumbling modes.

Figure 3:
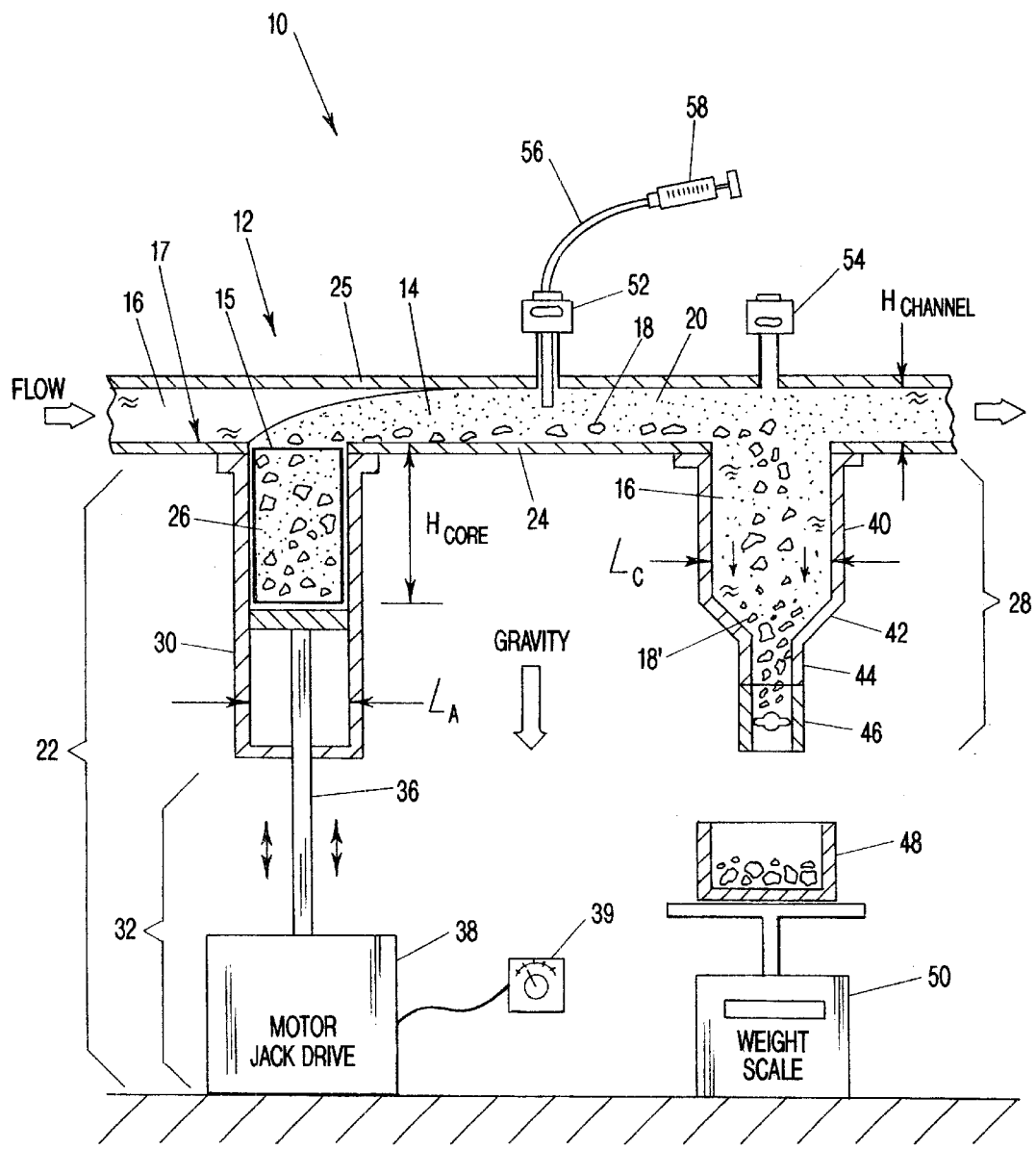
FIG. 3 shows a schematic side view of a cross-section of an adjustable shear stress erosion and transport (ASSET) flume, according to an embodiment of the present invention.

FIG. 3 shows a schematic side view of a cross-section of an adjustable shear stress erosion and transport (ASSET) flume, according to an embodiment of the present invention. Apparatus 10 comprises channel 12 for conveying a stream of flowing fluid 14, and erosion means 22, attached to an opening in the bottom 24 of channel 12, for exposing a sediment core sample 26 to shear stresses applied by flowing fluid 14. The scouring (i.e., shearing) action of flow stream 14 erodes sediments from core sample 26 and introduces them into flow stream 14. These eroded sediments can include bedload sediments 18 and suspended sediments 20, both of which are transported down channel 12.

Apparatus 10 further comprises trapping means 28, attached to an opening in the bottom 24 of channel 12 at a location downstream from erosion means 22, for gravitationally separating transported eroded bedload sediments 18 from the flow stream 14 and capturing them.

Apparatus 10 can be oriented substantially horizontally with respect to gravity, as shown in FIG. 3, which would require a pump, gravity, or other means for forcing the flow of fluid 14 through channel 12. Alternatively, apparatus 10 can be oriented at a pitched angle relative to horizontal (not shown), which could be used with free-flowing, gravity-driven flow of fluid 14, e.g., from a dam spillway or culvert pipe. Normally the ASSET flume is oriented such that the long axis of core sample 26 is vertical, and also that the longitudinal axis (i.e., the direction of fluid flow) is horizontal. However, the ASSET flume can be tilted or rotated about its longitudinal axis (i.e., the direction of fluid flow) to a non-vertical orientation in order to simulate flow on the side of a riverbank. Apparatus 10 can be rigidly supported by well-known structural support means or structural framework (not shown). Apparatus 10 can be housed in a laboratory room, or provided as a mobile system that can be moved to a test site in the field, such as in a truck or flat bed trailer.

Channel means 12 can be an open or closed (i.e., internal) channel. If open, channel 12 can be a three-sided, "U"-shaped open channel with a rectangular or square cross-section, or a one-sided shape having a curved cross-section. If closed, channel 12 can be pipe, tube, or flume having a circular, oval, elliptical, square, or rectangular cross-section. Channel 12 can be made of an optically transparent material, such as glass, clear polycarbonate or clear acrylic plastic, to permit viewing of the eroding surface and flow conditions during operation. Channel 12 can comprise a single-piece pipe or tube, such as made by extrusion or casting. Alternatively, channel 12 can comprise an assembly of multiple plates (bottom member 24, top member 25, and/or sidewalls (not shown in this view)) that can be held together in an fluid-tight assembly by bolts used to compress gaskets, O-ring seals, or coilspring seals at the mating surfaces. Flow stream 14 inside of channel 12 can flow essentially at atmospheric pressure, or at elevated pressures by pressurizing channel 12 above atmospheric pressure to simulate the pressure conditions at the bottom of a lake, river, or ocean, etc. Channel 12 can have a rectangular cross-section, with a channel height, $H_{channel}$, from 2–5 cm. Alternatively, $H_{channel}$ can be approximately 5 cm. Alternatively, $H_{channel}$ can be greater than 2 cm. As will be discussed later, the height of channel 12 can be chosen to equal a substantial portion of the free stream's boundary layer thickness (e.g., 90%). The width of channel 12 can be approximately 10 cm. The width/height ratio can be 2:1 or greater.

A closed channel configuration for channel 12 can be used in conjunction with high flow rates to achieve high shear stresses up to and exceeding 10 N/m$^2$, applied to surface 15 of sediment core sample 26. The velocity of fluid 14 can be from 0.25 m/s to 2.5 m/s, or can be higher than 2.5 m/s to simulate, for example, the conditions of a flash flood, Fluid 14 can comprise a multi-phase mixture of a liquid 16 and eroded sediments (suspended, bedload, or both). Alternatively, fluid 14 can comprise a multi-phase mixture of a liquid 16 and externally-added particles (sand, pebbles, sediments, leaves, sticks, gravel, etc.). Liquid 16 can be any liquid phase material, such as water, seawater, river water, contaminated water, oil, gasoline, etc. We use the term "water" interchangeably with "any liquid phase material" in this specification, since the most common applications primarily use water. Likewise, we use the phrases "fluid 14" and "flow stream 14" interchangeably.

The flow of fluid 14 through channel 12 can be a once-through, single-pass design in an open-loop type of system, or it can be continuously recirculated in an open or closed-loop type system. In a single-pass, open-loop system the fluid 14 flowing past sediment core sample 26 would always be clean and have no entrained sediments. Alternatively, in a recirculated, open or closed-loop system, fluid 14 could comprise entrained sediments, whose concentration may increase over time, due to multiple passes past erosion means 22. Alternatively, other sources of sediments or particles (i.e., non-sedimentary particles, such as leaves, sticks, etc.) can be introduced or "injected" in channel 12 by additional means attached at various location along channel 12 (to be discussed later).

The flow of fluid 14 through channel 12 can be steady-state, continuous, transient, pulsed, repeatedly pulsed, oscillatory, steadily-increasing, steadily-decreasing, sinusoidal, wave-like, or any combination of these, necessary to simulate the real-world conditions (e.g., flash floods, wave action on a beach, or tidal currents combined with wave action in a harbor)

The shape of channel 12, as illustrated in FIG. 3, is essentially a straight section. However, channel 12 could also be curved in any manner necessary to simulate unusual flow conditions and/or hydrodynamic effects. For example, channel 12 could be curved in a way to simulate the complex multi-dimensional flow field of water around a bridge support post, pier, or piling in a river. A curved channel 12 can be used to artificially create a locally high pressure on surface 15 of sediment core sample 26 due to radial acceleration of fluid 14 in the curved channel geometry, potentially affecting the measured erosion rates for sediment core samples containing entrained gases (e.g., methane). Using a curved channel to a locally high pressure could eliminate the need to build a closed-loop, externally-pressured, closed recirculating flow loop. The costs of a curved channel would be less than that of an externally pressured closed system.

Erosion means 22 comprises a mechanism for pushing up sediment core sample 26 into flow stream 14. Erosion means 22 can comprise a coring tube 30, which can be attached to the bottom 24 of channel 12 with a removable bolt and gasket arrangement, or other type of removable, water-tight connection. Coring tube 30 can hold and support sediment core sample 26 while it is being pushed up (i.e., extruded) and urged (i.e., displaced) into flow stream 14 through an opening in the bottom of channel 12. In this sense, sediment core sample 26 has a "variable depth". The term "variable depth" describes three aspects of the present invention. Firstly, as sample 26 erodes during erosion testing, it's length naturally becomes shorter (i.e., the length varies over time). Secondly, the initial length (i.e. the starting length) of sediment core sample 26 does not need to be the same from test to test. It could start out, for example, as 10 cm long in one test, and then another sample could be installed for a second test that starts out with a 20 cm length (so long as it fits within the total length of coring tube 30). However, the overall length of coring tube 30 can be extended by adding extension tubes (not shown). Thirdly, the term "variable length" also refers to the possibility that sediment core sample 26 is not required to be homogenous, but, rather, can comprise a non-homogenous arrangement of multiple sediment layers, which vary through the depth of the sample (e.g., from sand to clay to sand plus pebbles, and so on), as might be found in a real sample taken from the field.

Coring tube 30 can have a circular, square, or rectangular cross section, and can be made of steel, or a clear glass or plastic material (for visualizing the sediment core sample 26). If rectangular, the horizontal length, LA, of coring tube 30 can be approximately 15 cm, and the width can essentially match the width of channel 12 (e.g., approximately 10 cm). If cylindrically-shaped, the diameter of coring tube 30 can be approximately 10 cm, and the vertical length (i.e., height) can be approximately 1 meter long. The vertical height of tube 30 can be made as long as necessary by attaching extension tube segments (not shown), to accommodate very tall core samples (e.g., up to and exceeding 1 meter). This adjustable feature is useful, for example, for studying the erosion of contaminants sorbed to sedimentary particles buried at depths of up to several meters in the bottom sediments of rivers, lakes, esturaries, and near-shore areas of the oceans.

Erosion means 22 can further comprise vertical drive means 32 for pushing up or urging the upper surface 15 of sediment core sample 26 into contact with flow stream 14 during testing. Drive means 32 can comprise a piston and piston rod assembly 36 disposed inside of coring tube 30, which pushes on the bottom of core sediment sample 26, and is driven up or down by motorized jack drive 38 (e.g., worm gear, scissor-jack drive, stepper motor, hydraulic piston, pneumatic piston, linear motor, etc.). Displacement controller 39 can control the operation of jack drive 38, and, hence, control the vertical displacement of piston assembly 36 and sediment core sample 26. With appropriate gearing, a vertical position accuracy of +/−0.25 mm can be achieved. The bulk (i.e., total) erosion rate can be determined from the upward movement of sediment core sample 26 inside of coring tube 30 over a known period of time, as measured by changes in the vertical length of sediment core sample 26, $H_{core}$. Erosion means 22 can further comprise displacement measuring means (not shown) for measuring $H_{core}$ or for measuring the displacement of piston assembly 36 (such as a calibrated ruler, optical length tape scale encoder device, linear transducer means (LVDT), interferometry, etc.).

A variety of modes of operating vertical drive means 32 can be used. In one mode, an operator adjusts displacement controller 39 in such a way that the surface 15 of core sample 26 remains closely flush, level, or even with lower surface 17 of channel 12 (i.e., the bed of the channel) during erosion tests. In other words, as the vertical length of core sample 26 ($H_{core}$) decreases due to bulk erosion, the operator (or computer program) can continuously adjust the vertical position of piston assembly 36 to maintain surface 15 of sediment core sample 26 level with the bottom surface 17 of channel 12.

An alternative mode of operation is to continuously maintain the surface 15 of sediment core sample 26 at a fixed step height (e.g., 1 mm) above channel bed surface 17 during erosion tests, as described in U.S. Pat. No. 6,260,409 to Briaud, et al., which is herein incorporated by reference.

Sediment core sample 26 can comprise a real-world sample of actual sediments taken directly from the bottom of a lake, river, etc. Alternatively, sediment core sample 26 can be artificially prepared in the laboratory, by placing mixtures of water and particles into coring tube 30 and allowing the mixture to settle and consolidate for a sufficient period of time (e.g., 1–100 days).

Referring still to FIG. 3, trapping means 28 comprises means to collect and trap eroded sediments that fall due to gravity through an opening in the bottom of channel 12. These particles can fall into capture basin 40, which is attached to the bottom of channel 12. Alternatively, basin 40 can be made as an integral part of channel 12. Basin 40 can be removeably attached to channel 12. Trapping means 28 can be designed to primarily capture or trap bedload sediments (which travel along bottom surface 17 of channel 12). Eroded suspended sediments 20, on the other hand, are not captured because they stay suspended and travel past the trap. The downstream length, $L_c$, of capture basin 40, can be selected to be sufficiently long so as to catch bedload particles which start out at their maximum height (e.g., three grain diameters above surface 17) at the upstream edge of basin 40. Selection of the minimum required horizontal length ($L_c$) of basin 40 involves consideration of both the horizontal velocity of bedload particle 18 (which can't be more than the flow velocity of fluid 14), and vertical speed at which bedload particle 18 sinks or falls through fluid 14 (e.g., using Stoke's Law), over a distance of three grain diameters. Accordingly, capture basin 40 can have a rectangular cross section, with a length ($L_c$) of approximately 15 cm, and with a width that matches the width of channel 12 (e.g., approximately 10 cm). The vertical length of trapping means 28 can be sufficient to collect all of the anticipated amount of bedload sediments collected during a normal test period.

Capture basin 40 can have a lower section with inwardly-tapered side-walls 42, which serves to funnel the collected bedload particles 18' into a collection region 44. A valve 46 can be attached to the open lower end of collection region 44, for draining out the accumulated bedload particles 18' (and overlying fluid) at selected intervals during testing (even while fluid 14 is flowing). Valve 46 can be a 2" ball or butterfly valve.

After a fixed period of erosion time, the accumulated bedload particles 18' collected in collection region 44 can be drained into container 48 by opening valve 46. The overlying water in container 48 can be poured off, and then container 48 can be placed in an oven for drying. After drying, container 48 can be weighed with scale 50 to determine the weight of collected bedload sediments 18'.

Referring still to FIG. 3, a plurality of small valves 52, 54 can be placed through upper surface 25 of channel 12 at various flume locations, which penetrate through the channel's wall. Opening of these valves subsequently exposes the interior of the flow channel (if a closed channel) to atmospheric pressure at those locations. This can be used to prevent negative pressures (i.e., less than atmospheric) from developing at erosion means 22 and/or at trapping means 28, when apparatus 10 is operated at high flow velocities (and, hence, high shear stress), due to large pressure drops along the channel. Internal pressures less than atmospheric can (undesirably) pull up sediment core sample 26 too fast, or uncontrollably, into flow stream 14.

Valves 52 or 54 can also be used to hold and seal a short length of small diameter plastic tubing 56 (e.g., Tygon™ tubing), which can be placed through the center of the valve's body and then into the middle of channel 12 to take a sample of fluid 14 during testing. The sample of fluid can be collected by using a syringe 58 attached to the end of tubing 56 to suck out a small volume of liquid. Approximately 150–300 ml of fluid can be sampled this way, and then filtered with a 0.2 micron filter paper using a vacuum pump system. Then, the filter paper can be dried and weighed. This can then be used to determine the concentration, C, of eroded suspended sediments in the bulk of fluid 14 by dividing the weight of the dry sediment by the volume of fluid sampled by syringe 58.

Figure 1:
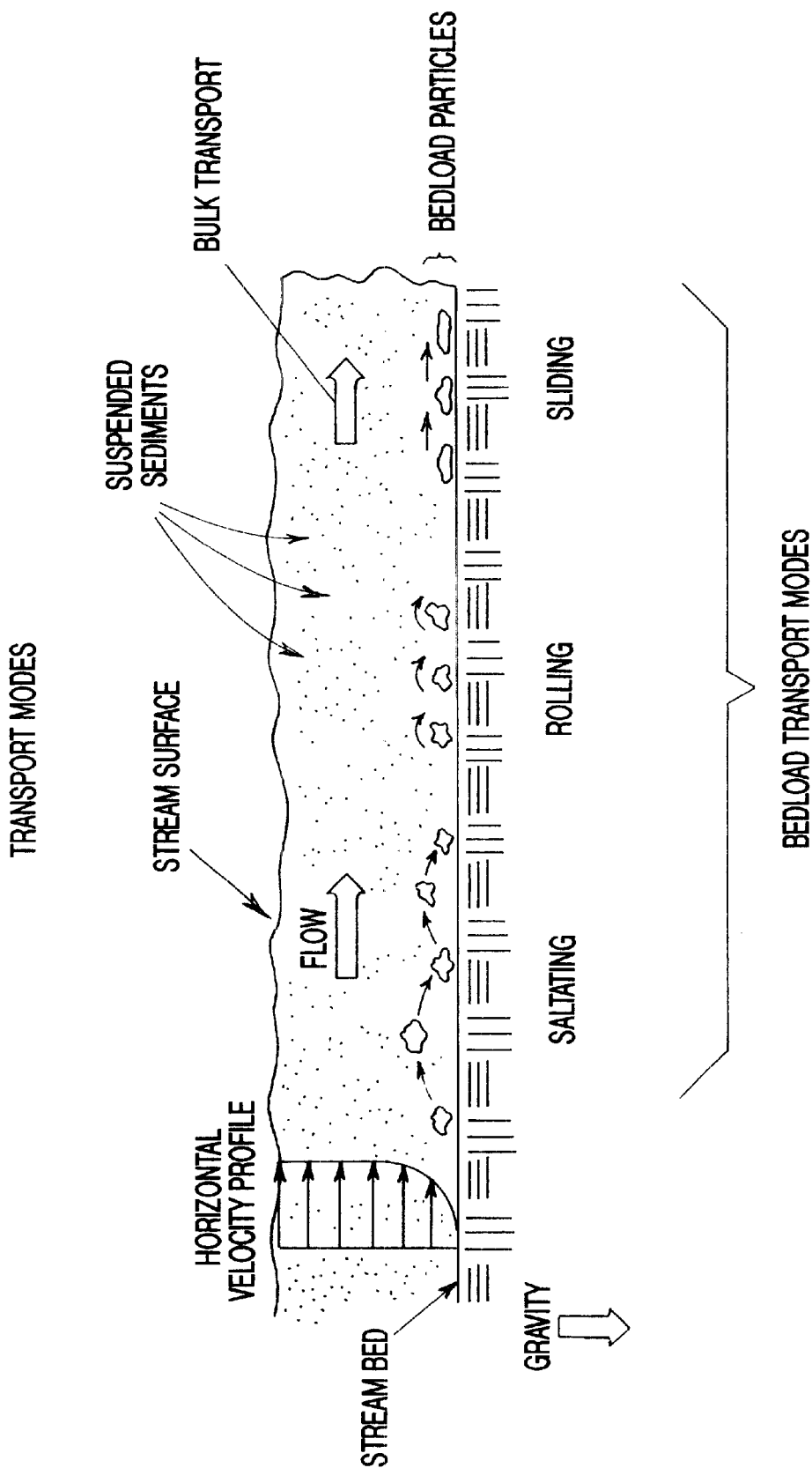
FIG. 1 shows a schematic side view of a streambed with flowing water causing erosion of sediments, illustrating the difference between suspended and bedload transport of eroded sediments.
Figure 2:
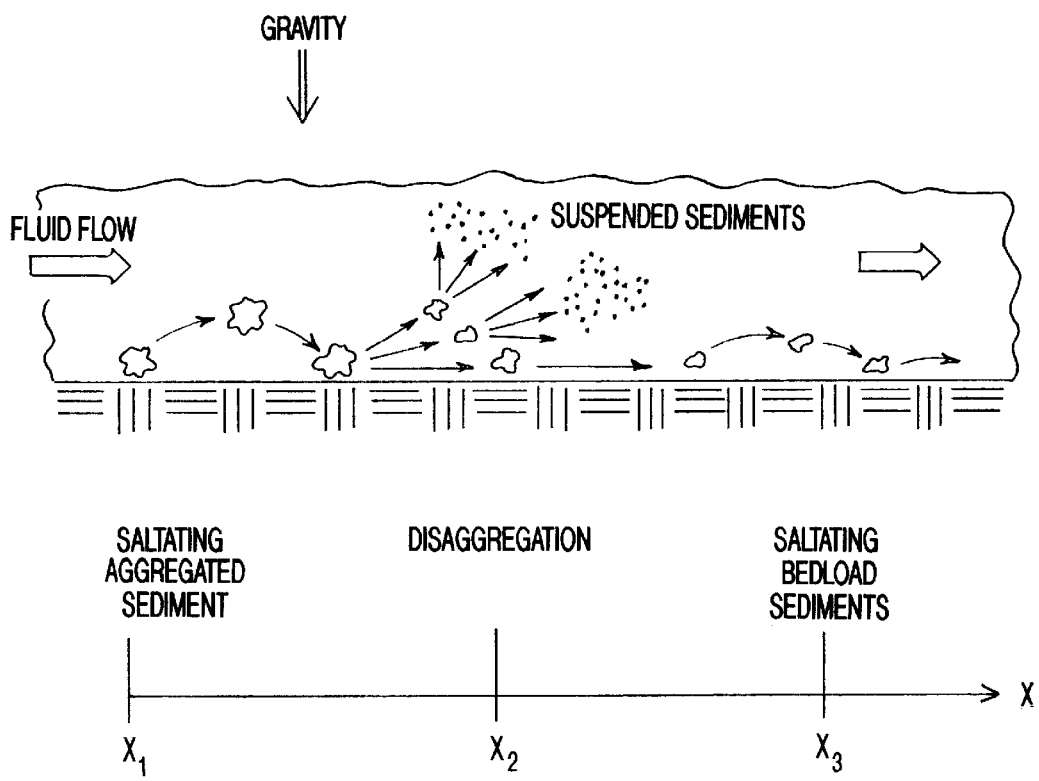
FIG. 2 shows a schematic side view of a stream bed with flowing water eroding sediments, illustrating how a saltating, aggregated sediment particle that was eroded at position $X_1$ can disaggregate into smaller particles at a downstream location, $X_2$; wherein the smaller particles can subsequently be transported either as suspended sediments or as bedload sediments.
Figure 4A:
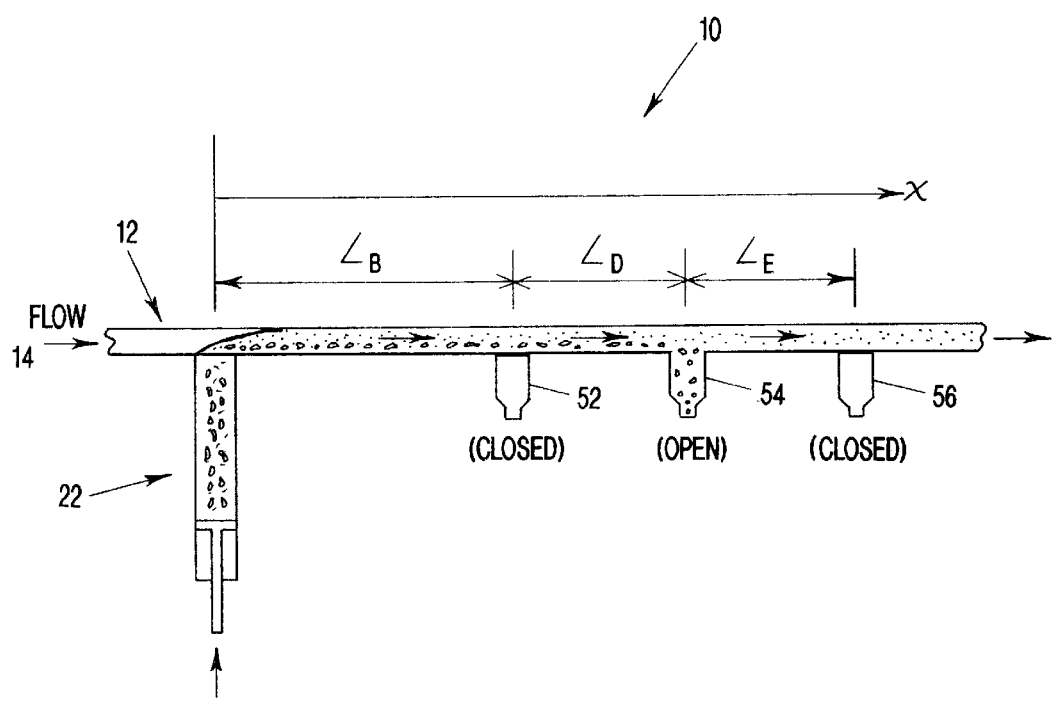
FIG. 4A shows a schematic side view of a cross-section of an adjustable shear stress erosion and transport (ASSET) flume with multiple traps, according to an embodiment of the present invention.

FIG. 4A shows a schematic side view of a cross-section of an adjustable shear stress erosion and transport (ASSET) flume with multiple traps, according to an embodiment of the present invention. In this embodiment, three traps, 52, 54, and 56 are disposed downstream of erosion means 22. The horizontal distances between the first trap 52 and erosion means 22 ($L_B$), and the spacing between adjacent traps, $L_D$ and $L_E$, can be chosen according to the requirements of the erosion test program. Alternatively, $L_B$, $L_D$, and $L_E$, can be approximately one meter. Traps 52, 54, and 56 can be open or closed during testing (e.g., by a closure plate across the top of the trap). For example, in FIG. 4 traps 52 and 56 are closed, while trap 54 is open. The various permutations of open/closed traps, and the number of downstream traps, can be selected to measure properties associated with the disaggregation of eroded bedload sediments 18 during transport down the channel (see FIG. 2). One possible sequence is as follows. A series of three erosion tests are performed, using identical sediment core samples 26, the same flow conditions, and the same period of erosion time. In the first test, trap 52 is open and the other two are closed. In the second test, trap 54 is open and the other two are closed. Finally, in the third test, trap 56 is open and the other two are closed. Comparison of the results from the three tests can be used to provide a useful measure of the disaggregation rate of bedload particles as a function of the length of travel downstream.

Figure 4B:
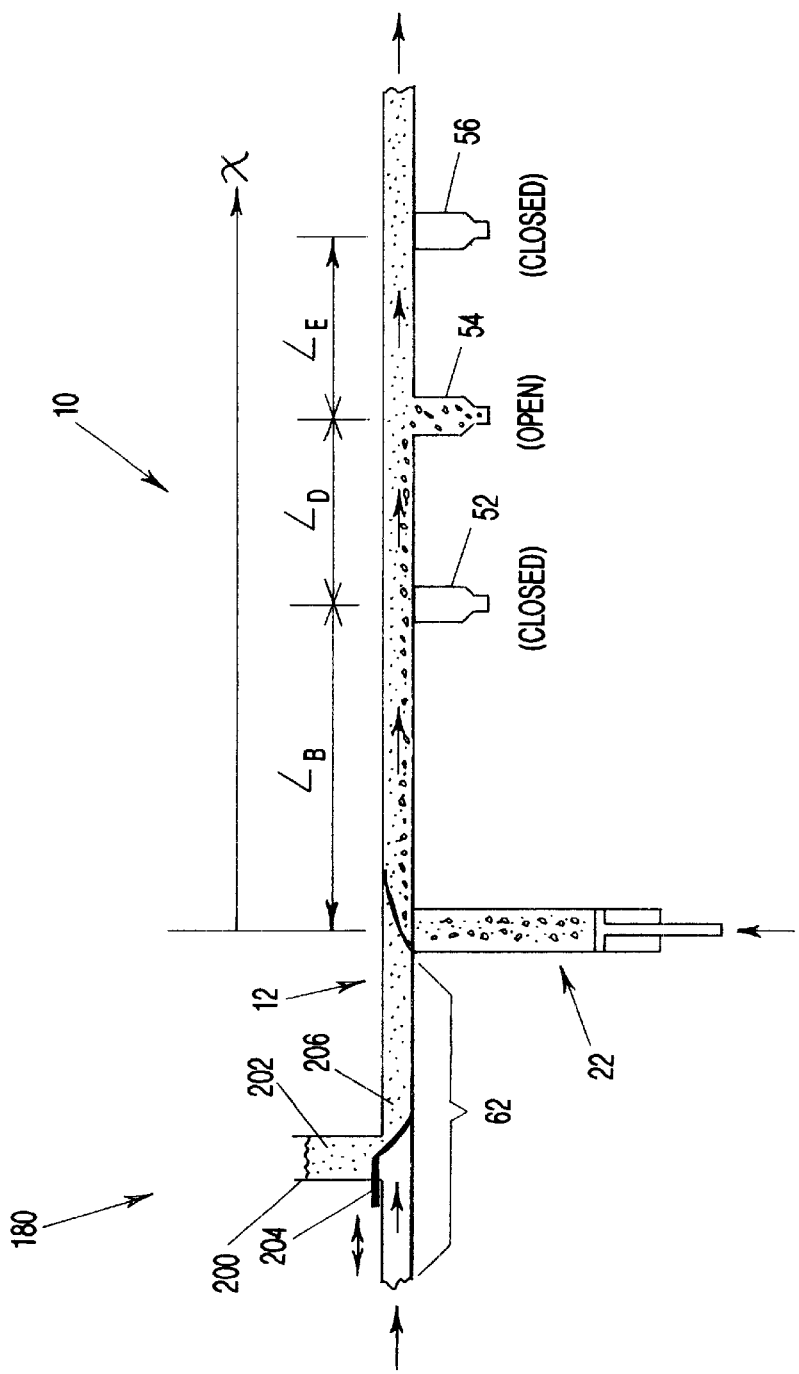
FIG. 4B shows a schematic side view of a cross-section of an adjustable shear stress erosion and transport (ASSET) flume with multiple traps, and with an upstream sediment injector, according to an embodiment of the present invention.

FIG. 4B shows a schematic side view of a cross-section of an adjustable shear stress erosion and transport (ASSET) flume with multiple traps, and with an upstream sediment injector, according to an embodiment of the present invention. This figure is identical to FIG. 4A, except for the addition of a sediment injector 180 attached to the upstream channel segment 62. Injector 180 can add (i.e., inject) sediments 202 into flow stream 14 at a position upstream of erosion means 22 for the purpose of providing a flowing fluid 206 that has entrained sediments 202 different than sediments eroded from sediment core sample 26. For example, core sample 26 might contain primarily clay-like sediments with small pebbles (5 mm), while sediments 202 might be beach sand. Use of sediment injector 180 thereby allows the composition of the flowing stream 14 to be adjusted and controlled independently from the composition of the sediment test section, providing enhanced flexibility for testing a wider variety of situations. Injector 180 can comprise a container (e.g. hopper) 200 for holding and dispersing sediments 202 into the top of flow stream 14 through an opening in the upper surface of channel 12. Control means 204 can be used to control the gravity flow of sediments 202 into flow stream 14. Control means 204 can be a sliding door (as shown in FIG. 4B), an adjustable iris, or other valve-like mechanism well known to those skilled in the art. Sediment 202 is not limited to a single type of particle, and can comprise mixed particles or objects, such as sand plus leaves, or pebbles plus small sticks, or sand plus gravel.

Figure 4C:
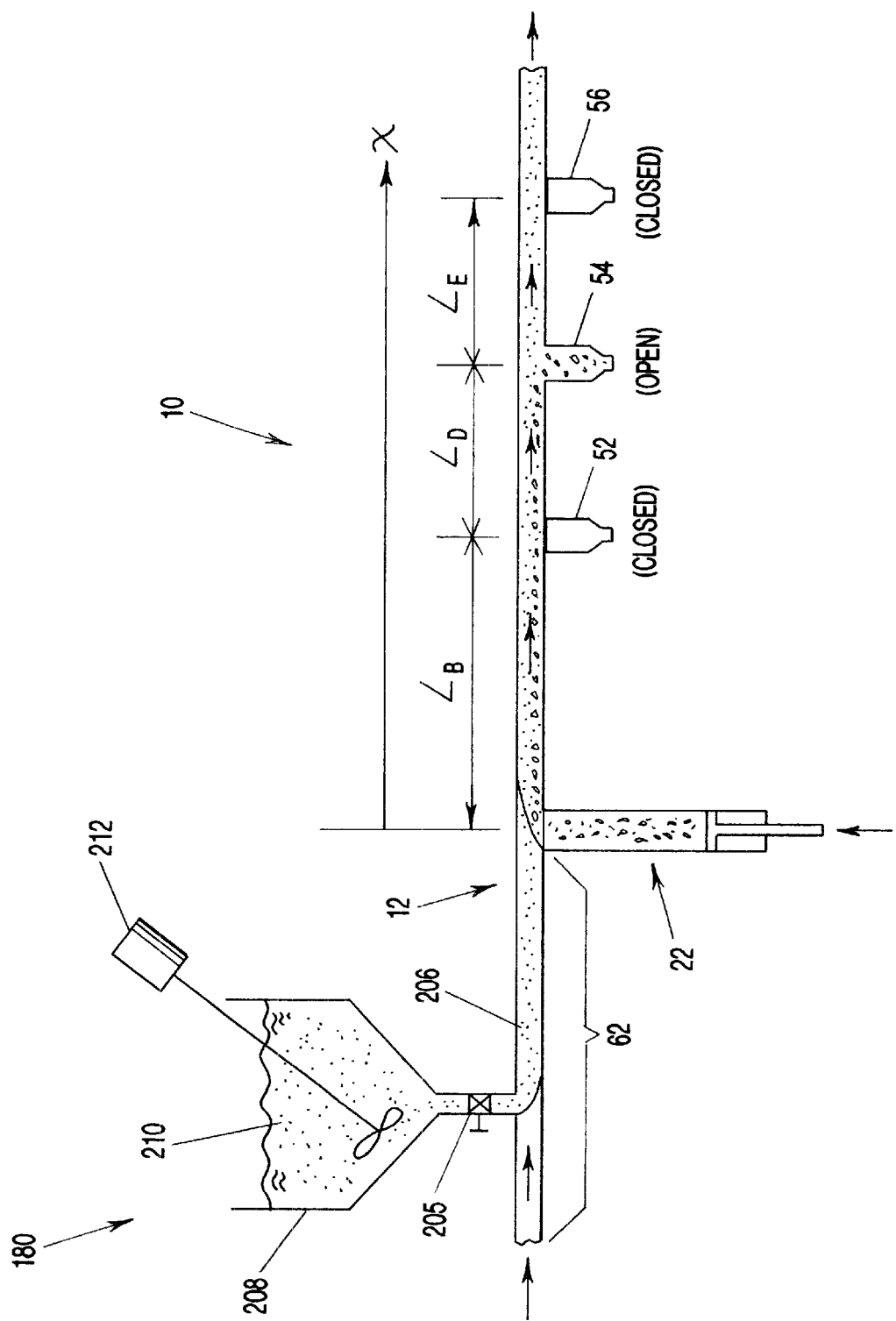
FIG. 4C shows a schematic side view of a cross-section of an adjustable shear stress erosion and transport (ASSET) flume with multiple traps, and with an upstream sediment injector, according to an embodiment of the present invention.

FIG. 4C shows a schematic side view of a cross-section of an adjustable shear stress erosion and transport (ASSET) flume with multiple traps, and with an upstream sediment injector, according to an embodiment of the present invention. This figure is similar to FIG. 4B, except that sediment injector 180 comprises a holding tank 208 in place of hopper 200. Tank 208 comprises water and sediments 202, that when mixed with blended 212, form a mixture 210 of sediments suspended in water. Mixture 210 can be added to flow stream 14 in upstream section 62 by opening valve 205.

Figure 4D:
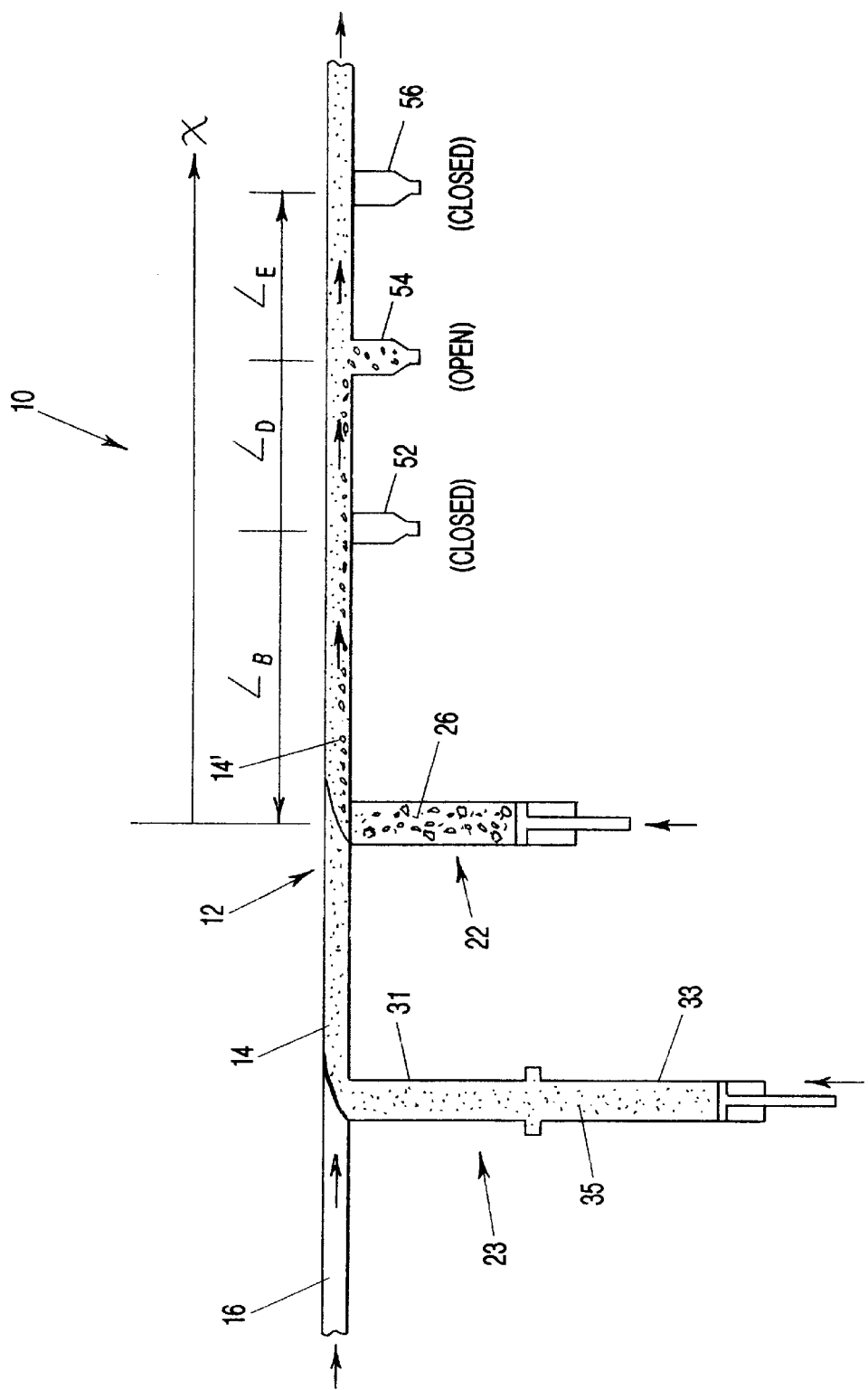
FIG. 4D shows a schematic side view of a cross-section of an adjustable shear stress erosion and transport (ASSET) flume, with two erosion test sections, and with multiple traps, according to an embodiment of the present invention.

FIG. 4D shows a schematic side view of a cross-section of an adjustable shear stress erosion and transport (ASSET) flume, with two erosion means, and with multiple traps, according to an embodiment of the present invention. The use of two erosion means, downstream erosion means 22 and upstream erosion means 23, placed in series allows for greater flexibility in providing a more complex mixture of particles transported in flow stream 14 before it encounters sample 26. FIG. 4D also illustrates the option of providing a longer sediment core sample 35 by attaching a second core tube 33 to extend the length of the first core tube 31. The rates with which core samples 35 and 26 are pushed up during testing can be same, or different, depending on the conditions, since the materials contained in the two different core samples can be different.

FIG. 5A shows a schematic elevation view of an adjustable shear stress erosion and transport (ASSET) flume with multiple traps and a rectangularly-shaped sediment core sample, according to an embodiment of the present invention. Channel 12 can have a width of approximately 10 cm. Trap channel 70 is located downstream of erosion test section 80. Erosion test section 80 comprises an upstream length of straight channel 62 just before sediment core sample 26, and a downstream section 63 between sample 26 and first trap 52. The upstream length of straight channel 62 can be sufficiently long to permit fully-developed turbulent flow to exist in test section 80, and in particular, at the downstream end of section 62 (i.e., at the location of sediment core sample 26). In this embodiment, the upstream length of straight channel 62 can be approximately 200 cm. Alternatively, the upstream length can be chosen to be greater than or equal to twenty-five times the channel's hydraulic diameter. The distance between sediment erosion sample 26 and the first trap 52, and between adjacent traps 52, 54, 56, can be approximately 1 meter. Upstream of erosion test section 80 is a flow converter segment that converts flow in round pipe 58 (e.g., 2") to flow in a rectangular channel 12 (e.g. 10 cm wide×5 cm high).

FIG. 5B shows a schematic elevation view of an adjustable shear stress erosion and transport (ASSET) flume with multiple traps and a cylindrically-shaped sediment core sample, according to an embodiment of the present invention. In this embodiment, sediment core sample 26 is circular with a diameter, for example, of approximately 10 cm.

Figure 6:
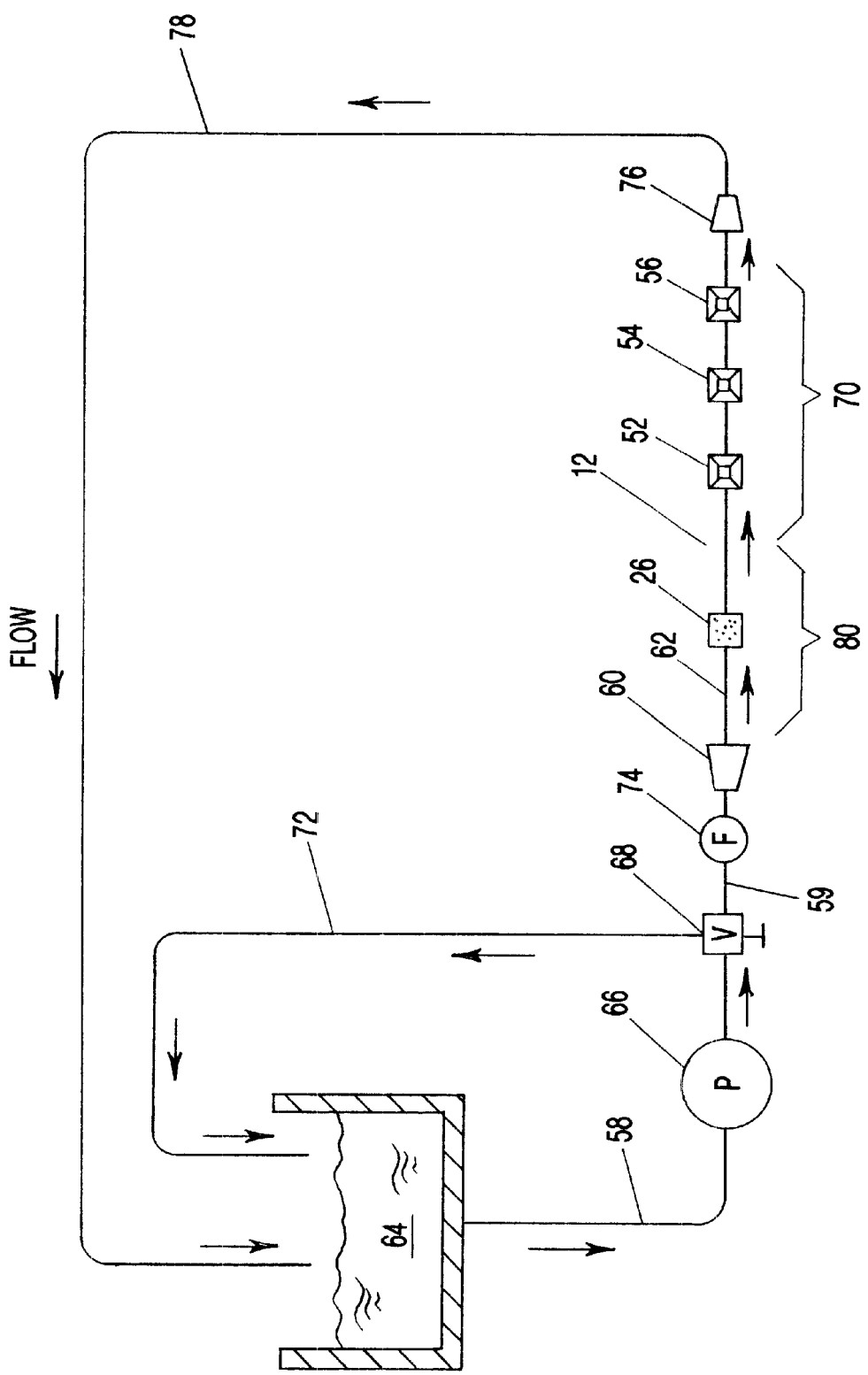
FIG. 6 shows a schematic diagram of the recirculating flow system for an adjustable shear stress erosion and transport (ASSET) flume with multiple traps, according to an embodiment of the present invention.

FIG. 6 shows a schematic diagram of a recirculated, open loop flow system for an adjustable shear stress erosion and transport (ASSET) flume with multiple traps, according to an embodiment of the present invention. Water (or other liquid 16) is stored in storage tank 64, which can have 120 gallon capacity. Water flows through inlet pipe 58 to pump 66. Pump 66 can be a 180 gallon per minute centrifugal pump, or a positive displacement pump. The speed of pump 66 can be changed to increase or decrease the velocity of flow stream 14. Hence, the shear stress is "adjustable" by changing the flow velocity.

In one test mode, the velocity of the flow stream 14, and, hence, speed of pump 66, is held constant during a single erosion and transport test. However, in another test mode, the velocity of stream 14 can be varied during the test, for example, by increasing or decreasing the pump's speed during the test, or by turning pump 66 on and off during the test. In another embodiment, pump 66 can comprise a peristaltic pump, which uses a mechanical action to compress compressible tubing (or hose) to create a wave-like pulsation of the flow rate, useful for simulating wave-action.

Next, water flows from pump 66 to 3-way diverter valve 68, which can divert some or all of the flow stream into a bypass pipe 72, which dumps back into tank 64. Pipe 58 and 72 can be 2" diameter. Water from valve 68 flows through a flowmeter 74 and into upstream flow converter section 60, which converts the cross-section from circular (e.g. 2") to rectangular (e.g. 10 cm×5 cm). Water then flows through erosion test section 80 and downstream trap channel 70, where it passes through downstream flow converter 76, which changes the cross-section back to circular, where water flows through return pipe 78 to tank 64. Pipe 78 can be 3" diameter.

FIGS. 7A–7K illustrate various embodiments of internal baffle designs that can be used inside of capture basin 40 with trapping means 28. Internal baffles can be used to create a quiescent flow condition that will minimize interference with the hydrodynamics and velocity vectors of the main flow stream 14, especially above capture basin 40 at the trap/channel interface, and immediately downstream thereof. Internal baffles can also be used to increase the trapping efficiency, by preventing re-circulation zones from ejecting bedload sediments out of the trap and back into the main flow stream 14.

Figure 7A:
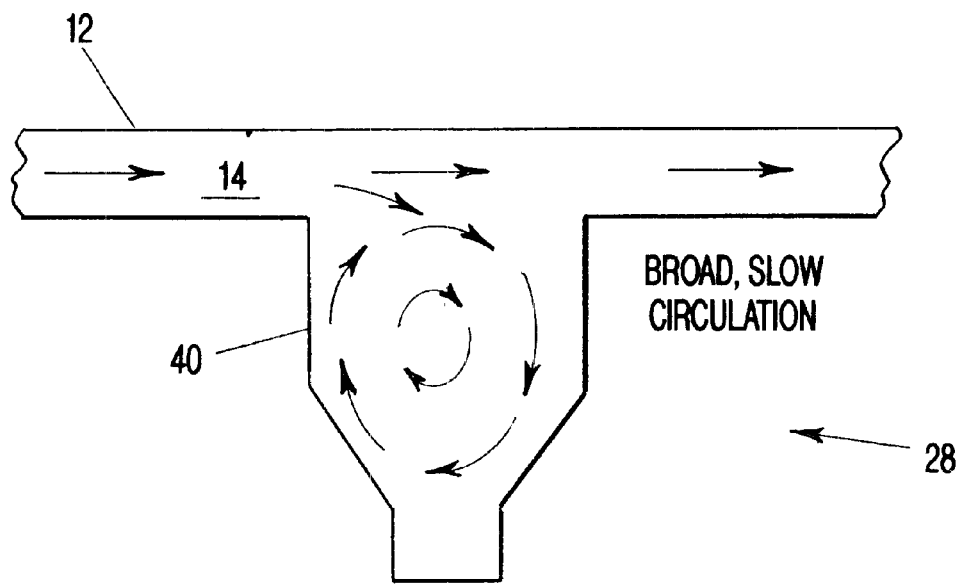
FIG. 7A shows a schematic side view of a trap attached to a trap channel, without internal baffles, according to an embodiment of the present invention.

FIG. 7A shows a schematic side view of a trap attached to a trap channel, without any internal baffles, according to an embodiment of the present invention. In this case, a broad, slow circulation pattern can develop inside of capture basin 40. Depending on the magnitude of the vertical velocity vectors on the upstream side of basin 40, incoming bedload sediments 18 may or may not be ejected back into the main flow stream 14.

Figure 7B:
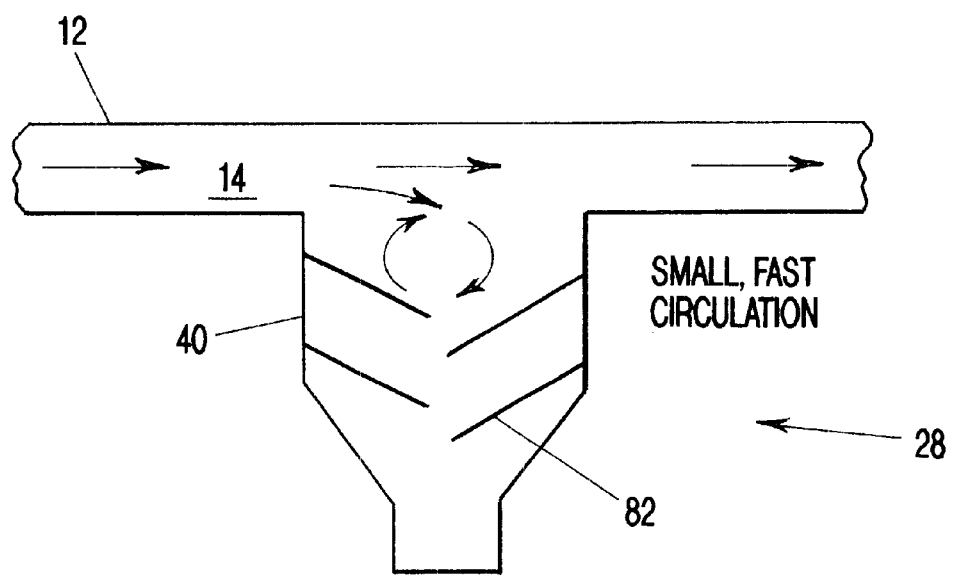
FIG. 7B shows a schematic side view of a trap attached to a trap channel, with internal baffles, according to an embodiment of the present invention.

FIG. 7B shows a schematic side view of a trap attached to a trap channel, with internal baffles, according to an embodiment of the present invention. Here, angled baffles 82 are attached to the sidewalls of basin 40, and are angled downwards to permit particles to slide or roll down the ramps. With long baffles 82 (as illustrated in FIG. 7B) a small, fast circulation zone can develop at the top of basin 40 that can eject or propel particles back out of the trap and back into the main flow stream 14, thereby decreasing overall trapping efficiency. The small, fast circulation zone can also perturb the overlying main flow stream 14 near the trap/channel interface.

Figure 7C:
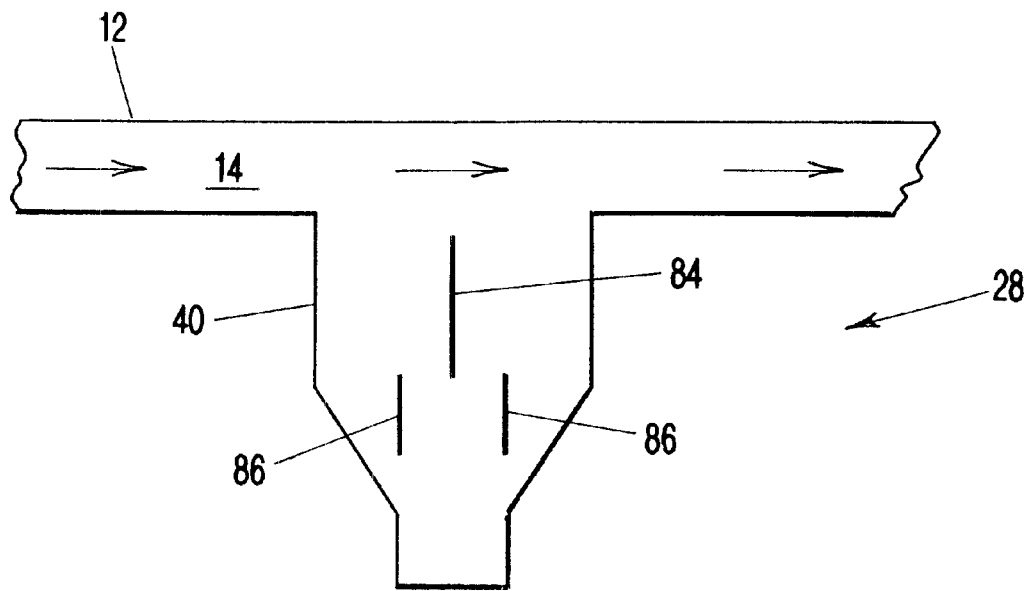
FIG. 7C shows a schematic side view of a trap attached to a trap channel, with internal baffles, according to an embodiment of the present invention.

FIG. 7C shows a schematic side view of a trap attached to a trap channel, with internal baffles, according to an embodiment of the present invention. A long, vertical baffle 84 is placed along the centerline of basin 40 in the basin's upper half, and two, short vertical baffles 86 are placed in the lower half of basin 40 on either side of the centerline. This baffle configuration can disrupt and inhibit the circulation pattern shown in FIG. 7A, and increase trapping efficiency.

Figure 7D:
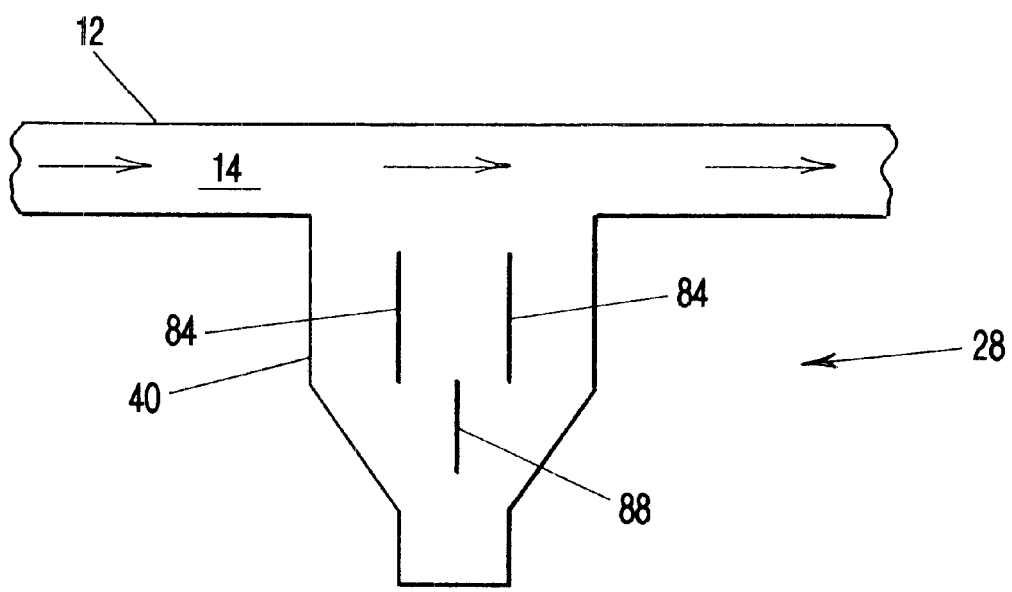
FIG. 7D shows a schematic side view of a trap attached to a trap channel, with internal baffles, according to an embodiment of the present invention.

FIG. 7D shows a schematic side view of a trap attached to a trap channel, with internal baffles, according to an embodiment of the present invention. Two long, vertical baffles 84 are placed on either side of the centerline of basin 40 in the basin's upper half, and one, long vertical baffle 84 is placed in the lower half of basin 40 along the centerline. This baffle configuration can disrupt and inhibit the circulation pattern shown in FIG. 7A, and increase trapping efficiency.

Figure 7E:
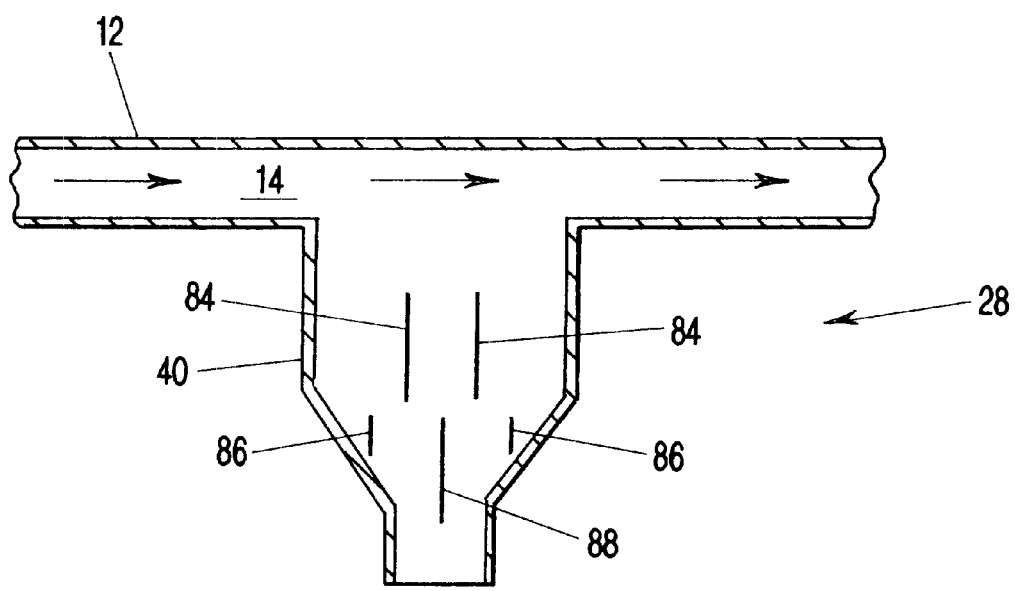
FIG. 7E shows a schematic side view of a trap attached to a trap channel, with internal baffles, according to an embodiment of the present invention.

FIG. 7E shows a schematic side view of a trap attached to a trap channel, with internal baffles, according to an embodiment of the present invention. Two long, vertical baffles 84 are placed on either side of the centerline of basin 40 in the basin's upper half, and one, long vertical baffle 84 is placed in the lower half of basin 40 along the centerline. Additionally, two, short vertical baffles 86 are placed on either side of the centerline in the lower half of basin 40. This baffle configuration can disrupt and inhibit the circulation pattern shown in FIG. 7A, and increase trapping efficiency.

Figure 7F:
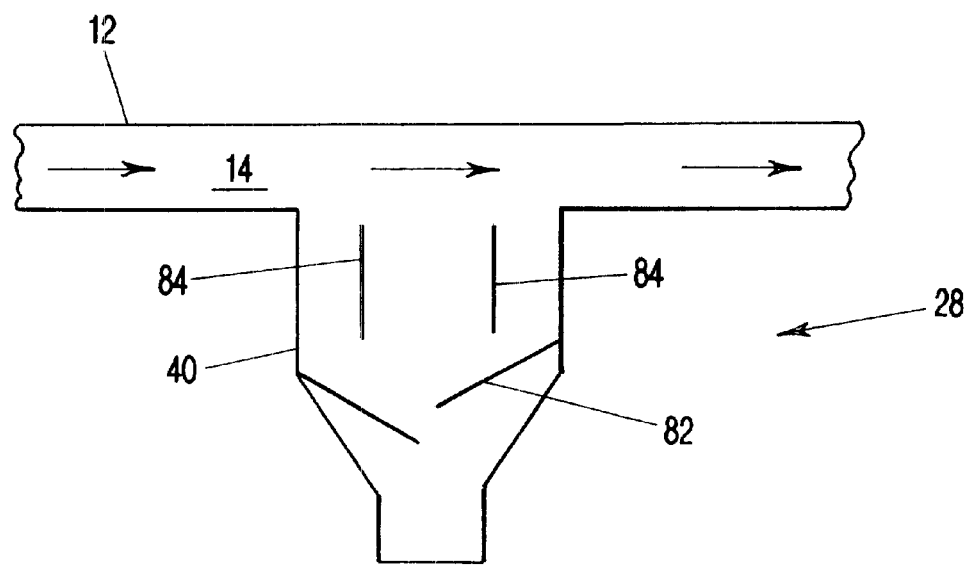
FIG. 7F shows a schematic side view of a trap attached to a trap channel, with internal baffles, according to an embodiment of the present invention.

FIG. 7F shows a schematic side view of a trap attached to a trap channel, with internal baffles, according to an embodiment of the present invention. Two long, vertical baffles 84 are placed on either side of the centerline of basin 40 in the basin's upper half, and two angled baffles 82 are placed in the lower half of basin 40, angled downwards.

Figure 7G:
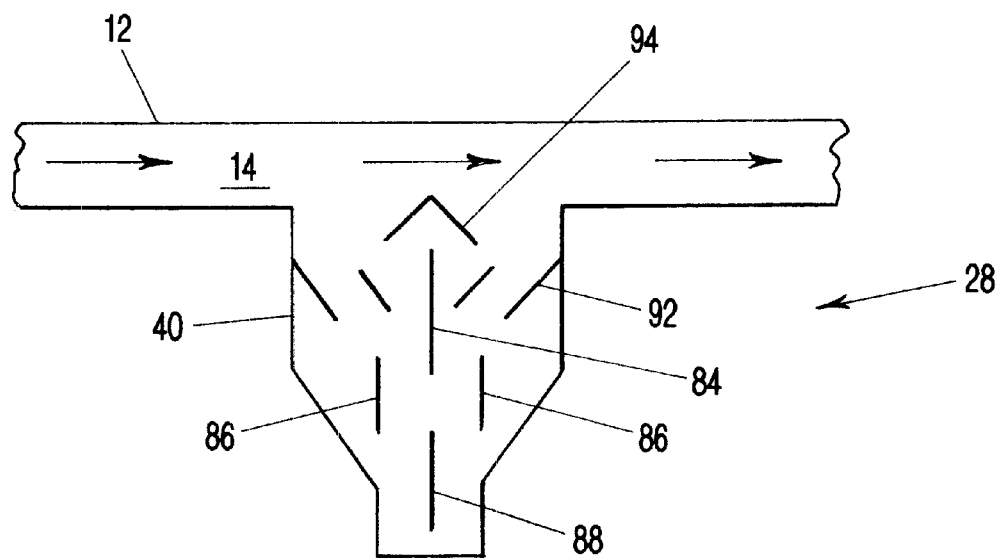
FIG. 7G shows a schematic side view of a trap attached to a trap channel, with internal baffles, according to an embodiment of the present invention.

FIG. 7G shows a schematic side view of a trap attached to a trap channel, with internal baffles, according to an embodiment of the present invention. A long, vertical baffle 84 is placed along the centerline of basin 40 in the basin's upper half, and another long, vertical baffle 84 is placed along the centerline of basin 40 in the basin's lower half. Two, short vertical baffles 86 are placed in the lower half of basin 40 on either side of the centerline. Four, short, angled baffles 92 are placed at 45 degrees inclination in the upper half of basin 40, on either side of the centerline. Additionally, an inverted chevron-shaped baffle 94 is placed along the centerline near the top of basin 40. This baffle configuration can disrupt and inhibit the circulation pattern shown in FIG. 7A, and increase trapping efficiency.

Figure 7H:
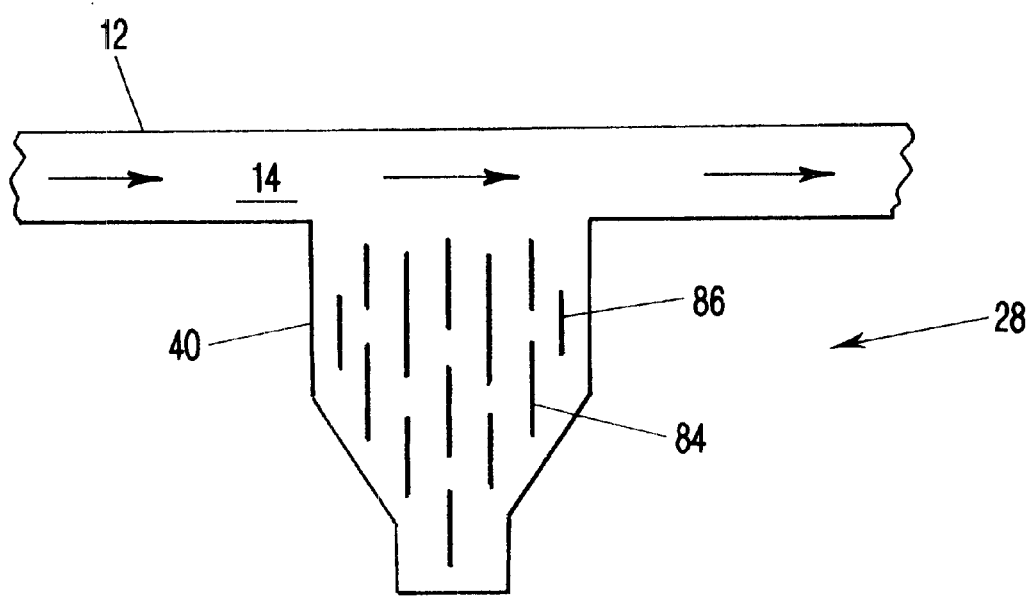
FIG. 7H shows a schematic side view of a trap attached to a trap channel, with internal baffles, according to an embodiment of the present invention.

FIG. 7H shows a schematic side view of a trap attached to a trap channel, with internal baffles, according to an embodiment of the present invention. A plurality of long vertical baffles 86 and short vertical baffles 84 are placed in an evenly spaced pattern that roughly fills up the volume within basin 40. This baffle configuration can disrupt and inhibit the circulation pattern shown in FIG. 7A, and increase trapping efficiency. The distance between adjacent baffles, however, cannot be so small as to prevent the free passage of the largest bedload sediments (e.g. 1 cm) as they fall through trap 28. This requirement limits the maximum number of vertical baffles that can be placed inside basin 40 using this pattern.

Figure 7I:
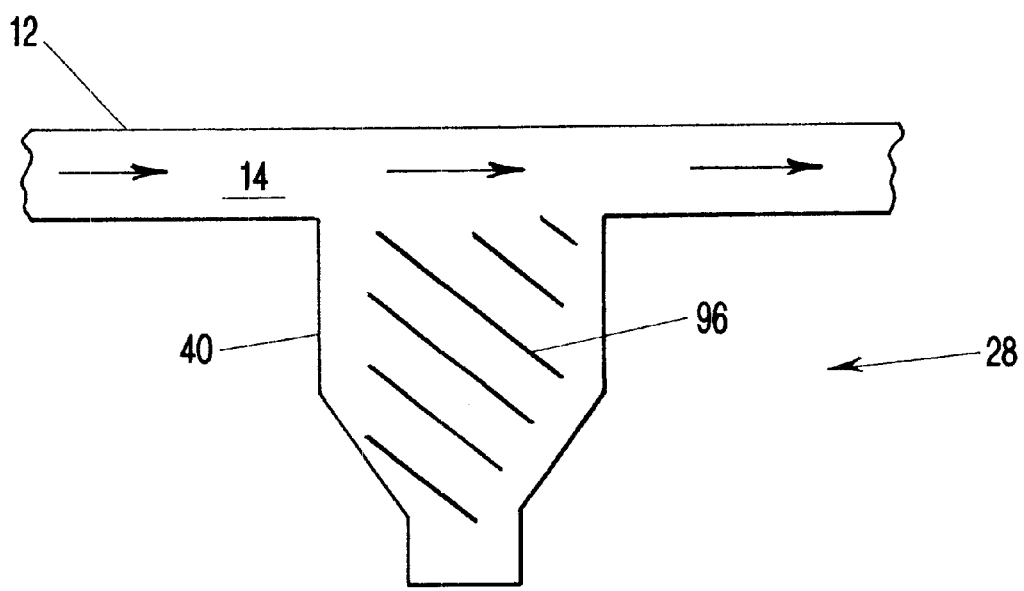
FIG. 7I shows a schematic side view of a trap attached to a trap channel, with internal baffles, according to an embodiment of the present invention.

FIG. 7I shows a schematic side view of a trap attached to a trap channel, with internal baffles, according to an embodiment of the present invention. A plurality of short and long angled baffles 96 are placed at roughly a 45 degree angle within basin 40. All of the baffles are parallel to each other, and evenly spaced apart. This baffle configuration can disrupt and inhibit the circulation pattern shown in FIG. 7A, and increase trapping efficiency. The distance between adjacent baffles, however, cannot be so small as to prevent the free passage of the largest bedload sediments (e.g. 1 cm) as they fall through trap 28. This requirement limits the maximum number of vertical baffles that can be placed inside basin 40 using this pattern. The trapping efficiency of this design likely depends on the direction of flow in flow stream 14, due to the asymmetry of the baffle configuration with respect to the centerline of basin 40.

Figure 7J:
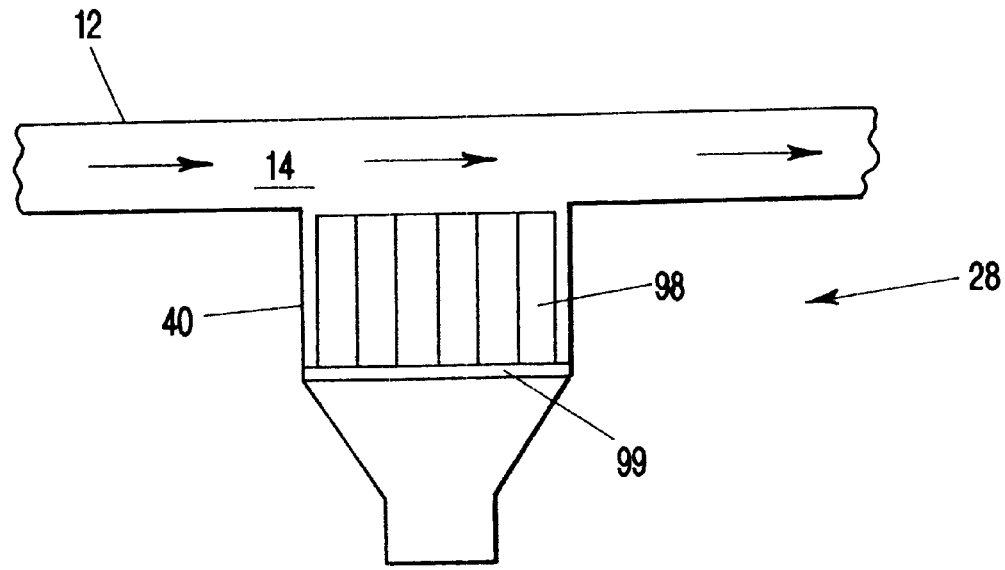
FIG. 7J shows a schematic side view of a trap attached to a trap channel, with internal baffles, according to an embodiment of the present invention.

FIG. 7J shows a schematic side view of a trap attached to a trap channel, with internal baffles, according to an embodiment of the present invention. Internal baffle 98 comprises a plurality of vertically oriented, stacked mini-channels, where the cross-section of each mini-channel can be circular, square, triangular, or hexagonal. If circular, the packing pattern of the mini-channels can be on a square grid, or hexagonal close packed (HCP). The plurality of stacked mini-channels 98 can be supported on a horizontal, perforated support plate 99 or grid-like support structure. This baffle configuration can disrupt and inhibit the circulation pattern shown in FIG. 7A, and increase trapping efficiency. The distance between adjacent walls in the stack, however, cannot be so small as to prevent the free passage of the largest bedload sediments (e.g. 1 cm) as they fall through trap 28. This requirement limits the maximum number of vertical walls, cells, or mini-channels that can be placed inside basin 40 using this design. The internal baffle structure 98 can be a honeycomb structure.

Figure 7K:
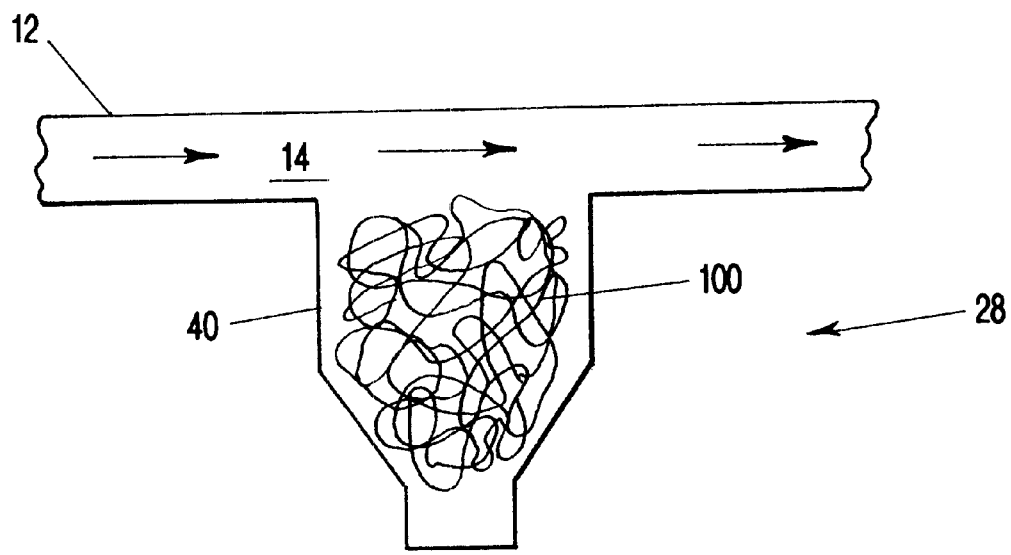
FIG. 7K shows a schematic side view of a trap attached to a trap channel, with an internal mesh, according to an embodiment of the present invention.

FIG. 7K shows a schematic side view of a trap attached to a trap channel, with an internal mesh, according to an embodiment of the present invention. Mesh 100 provides a plurality of surfaces that break up and disrupt circulation zones in a simple structure. The distance between adjacent surfaces in the mesh, however, cannot be so small as to prevent the free passage of the largest bedload sediments (e.g. 1 cm) as they fall through trap 28. This requirement limits the density of the mesh. Internal mesh 100 can be made of stainless steel wires.

Figure 8:
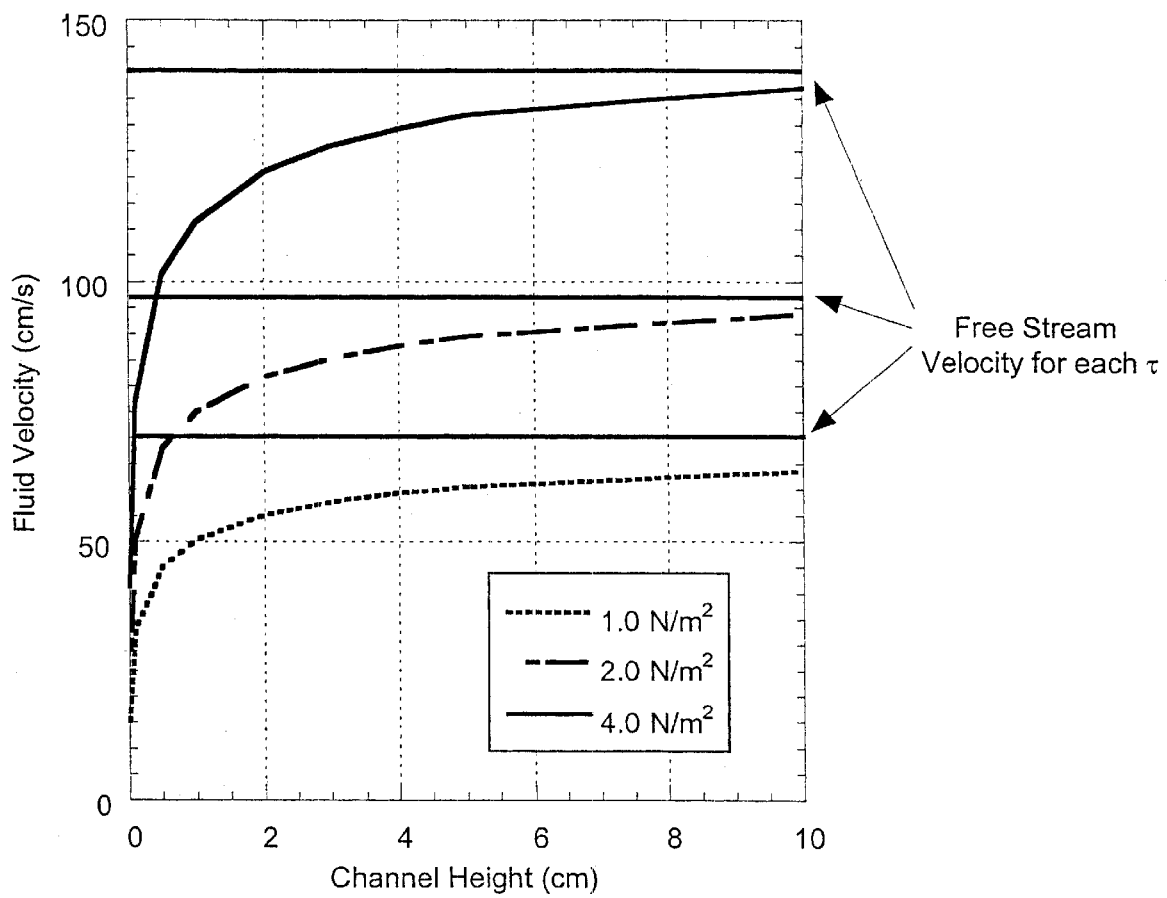
FIG. 8 plots the calculated mean fluid velocity as a function of channel height and flow shear stress, compared to the free stream surface velocity for each shear stress.

To accurately simulate the free stream conditions found in the field, the channel's height should be sufficiently tall. FIG. 8 plots the calculated mean fluid velocity as a function of channel height and flow shear stress, compared to the free stream surface velocity for each shear stress. For these flow conditions, 90% of the free stream (free surface) velocity can be achieved with a channel height greater than or equal to approximately 5 cm, for the range of shear stresses shown. With a channel height equal to 5 cm, the erosion test section can accommodate bedload particle sizes up to 1 cm in diameter without experiencing the upper boundary layer near the top surface of the channel.

For channel heights, $H_{channel}$, less than 5 cm (i.e. less that 90% of the free stream (free surface) velocity), a correction factor can be used to correct for the less-than-ideal boundary layer. This can be accomplished by creating a calibration curve of transport results using known, uniform quartz standards, e.g., from 20 to 1000 microns in size, as obtained by comparing test results between the reference $H_{channel}$=5 cm and $H_{channel}$<5 cm.

The method of using the present invention will now be described. With reference to FIGS. 3 and 6, the procedure for measuring the erosion rates of sediments as a function of shear stress and depth is as follows. Sediment erosion sample 26 (i.e., sediment core) is prepared either in the laboratory, or provided directly from the field. Sample 26 is placed inside of coring tube 30, and vertically positioned using jack means 32 until surface 15 of sample 26 is flush and level with bottom surface 17 of channel 12. Water (or other liquid 16) fills channel 12, and then pump 66 is turned on to provide a steady flow of water across the surface of sample 26. The flow rate is quickly increased, while reading flowmeter 74, to the desired flow rate (and shear stress). This can be accomplished by increasing the speed of pump 66, and/or by using 3-way valve 68 to divert flow from bypass pipe 72 into the mail flow pipe 59. Once a critical shear stress has been exceeded, erosion or scouring of sample 26 begins. The operator (or computer program) adjusts controller 38 to drive vertical drive means 32 in a manner so as to continually push sediment core sample 26 upwards at a rate sufficient to keep the sample's surface 15 flush or level with channel bottom surface 17. This extrusion rate can be continuously monitored and adjusted periodically if core sample 26 comprises multiple layers of varied sediments that erode at different rates. The vertical length, $H_{core}$, of the sediment core sample 26 is measured before and after the known time interval (i.e., period) for testing has elapsed. The average bulk erosion rate is calculated by taking the difference between successive measurements of $H_{core}$, and dividing by the time interval. The time interval can be chosen to be sufficiently long to erode 1 cm of material. During the test, the suspended load concentration can be sampled through tube 56 with syringe 58. At the end of each erosion test for each shear stress, the bedload traps can be emptied, and the tank emptied and filled with clean water. The flow can be adjusted to produce another value of shear stress, and the process repeated. The flow can be increased in-between runs.

The procedure for measuring the concentration, C, of eroded suspended sediments was described previously. After the suspended load concentration sample was collected, the pump can be turned off, and the system allowed to equilibrate. Then, the total volume of water in the system can be measured by using pre-calibrated markings on the side of storage tank 64. The total suspended load, S, is then given by multiplying the concentration, C, by the total volume of water in the system (including the tank and all of the plumbing in the flow loop).

After the suspended load concentration and total volume measurement in the system are sampled, the bedload traps can be drained of any overlying water. The contents of each trap can be placed into individual containers, dried in an oven at approximately 75 C., and then weighed. This gives the dry sediment weight that was transported as bedload and captured in each sediment trap.

Experimental Results

Tests were done to determine the transport characteristics after erosion for three pure quartz sediments with respect to shear stress. One quartz sediment was fine-grained (<30 μm), another was coarse-grained (>1 mm) and the third was a known mixture of the coarse and fine-grained quartz sediments. The mixture and fine grain sediments were individually mixed into a homogeneous composite prior to testing. The coarse-grained quartz sediment was mixed directly into the erosion core prior to testing. For each sediment type, rectangular cores were used for the erosion tests.

The fine-grained quartz sediment was prepared as follows. Approximately 100 lbs of dry quartz were placed in twelve-gallon cylindrical tanks and mixed with approximately 3 gallons of water until the sediment-water mixture was homogeneous. The sediment mixture was then poured to a depth of 30 cm in a coring tube. The core was allowed to consolidate for 2 days.

The mixture of fine-grained and coarse-grained quartz sediment was prepared as follows. 6,911 grams of the pre-mixed fine-grained quartz sediment (which is equivalent to 4713 grams of dry, fine-grained quartz) was mixed with 2,791 grams of coarse-grained quartz until the mixture was homogeneous. The resultant mixture was 37% coarse-grained and 63% fine-grained by mass. The sediment mixture was poured to a depth of 20 cm in a coring tube and allowed to consolidate for 2 days.

The coarse-grained quartz sediment used in these experiments was non-cohesive, settled quickly and could not be mixed in the manner described above. Therefore, the coarse-grained quartz sediment cores were prepared as follows. Water was poured directly into the core then dry quartz was placed into the water until the sediment water interface reached 30 cm. Since these quartz sediments were non-cohesive, density does not change appreciably with consolidation time. The core was allowed to consolidate for 1 day.

The procedure for measuring the erosion rates of the sediments as a function of shear stress and depth was as follows. The sediment cores were prepared as described above and then moved upward into the test section until the sediment surface was even with the bottom of the test section. A measurement was made of the depth to the bottom of the sediment in the core. The flume was then run at a specific flow rate corresponding to a particular shear stress. Erosion rates were obtained by measuring the remaining core length at different time intervals, taking the difference between each successive measurement, and dividing by the time interval.

In order to measure a meaningful concentration of bedload and suspended load at different shear stresses using only one core, the following procedure was generally used. Starting at a low shear stress, the flume was run sequentially at higher shear stresses with each succeeding shear stress being twice the previous one. For the purposes of these experiments, only one shear stress was run at a time. Each shear stress was run until at least 1 cm was eroded. The time interval was recorded for each run with a stopwatch. At the end of the erosion test for each shear stress, the bedload traps were emptied, the suspended load concentration was sampled, and the tank was emptied and filled with clean water. The flow was then increased to the next shear stress, and the process repeated.

The procedure for measuring the bedload and suspended load concentrations as a function of shear stress and depth was as follows. The erosion rates were measured as described above. In order to measure the suspended sediment concentration at the end of the erosion test approximately 150–300 ml of the overlying/re-circulating water was sampled before the pump was turned off. This sample was filtered with a 0.2 μm filter paper and vacuum pump system. The sample was dried and weighed. The suspended load concentration, C, is given by $$C = \frac{m_d}{V_s} \quad (1)$$

where $m_d$ is the dry sediment weight and $V_S$ is the volume sampled. After the suspended load concentration was sampled, the pump was turned off, the system was allowed to equilibrate and the total volume of water in the system was measured by the use of pre-calibrated markings on the side of the tank. The total suspended load, S, is then given by $$S=CV_T \tag{2}$$

where, C is defined above and $V_T$ is the total volume of water in the system after the erosion test (i.e. in the tank and all of the plumbing of the ASSET Flume).

After the suspended load concentration and total volume measurement in the system were sampled the bedload traps were drained of any overlying water. The contents of each trap were placed into individual containers, dried in an oven at approximately 75° C. and weighed. This gives the dry sediment weight that was transported as bedload and captured in each sediment trap.

The total eroded mass is the amount of solid particles from the sediment that are eroded and transported downstream as both bedload and suspended load. The total volume of sediment eroded, V, is defined by $$V=AD \tag{3}$$

where, A is the erosion surface area and D is the depth of sediment eroded. The total eroded mass is related to the bulk density, total volume and water content by $$M_T=\rho V(1-W) \tag{4}$$

where, $\rho$ and W are the bulk density and water content of the sediments respectively, both will be defined and described below.

For the analysis of the sediment bulk properties duplicate cores were prepared in the same manner as the rectangular erosion cores. The core sleeves of these analysis cores were made from 7.6 cm inner diameter thin acrylic tubes of the same length as the rectangular cores.

In order to determine the bulk density of the sediments at a particular depth and consolidation time, the sediment analysis cores were frozen, sliced into 2.5 cm sections, and then weighed (wet weight). They were then dried in the oven at approximately 75° C. for 2 days and weighed again (dry weight). The water content W is then given by $$W=\left(\frac{m_w-m_d}{m_w}\right) \tag{5}$$

where $m_w$ and $m_d$ are the wet and dry weights respectively. A volume of sediment, V, consists of both solid particles and water, and can be written as $$V=V_S+V_W \tag{6}$$

where $V_S$ is the volume of solid particles and $V_W$ is the volume of water. If the sediment particles and water have densities $\rho_S$ and $\rho_W$ respectively, the water content of the sediment can be written as $$W=\frac{\rho_w V_w}{\rho V} \tag{7}$$

where $\rho$ is the bulk density of the sediments. A mass balance of the volume of sediment gives $$\rho V=\rho_S V_S+\rho_W V_W \tag{8}$$

By combining Eqs. (6), (7), and (8), an explicit expression can be determined for the bulk density of the sediment, $\rho$, as a function of the water content, W, and the densities of the sediment particles and water. This equation is $$\rho=\frac{\rho_s\rho_w}{\rho_w+(\rho_s-\rho_w)W} \tag{9}$$

For the purpose of these calculations, it has been assumed that $\rho_S$=2.6 gm/cm$^3$ and $\rho_W$=1.0 gm/cm$^3$.

Particle sizes and particle size distributions were determined by use of a Malvern Mastersizer-S particle sizing package for particle diameters between 0.05 and 900 $\mu$m. The two natural sediments and the fine-grained quartz sediment samples had particle sizes less than 900 $\mu$m. Approximately 5 to 10 grams of sediment was placed in a beaker containing about 500 ml of water and mixed by means of a magnetic stir bar/plate combination. Approximately 1 ml of this solution was then inserted into the sizer's sampling system and further disaggregated as it was recirculated through the sampling system by means of a centrifugal pump. The sample was allowed to disaggregate for five minutes on the stir plate and an additional five minutes in the recirculating pump sampling system before analysis by the sizer. To ensure complete disaggregation and sample uniformity the sediment samples were analyzed and repeated in triplicate. From these measurements, the distribution of grain sizes and mean grain sizes as a function of depth were obtained. For the coarse-grained quartz sediment, which had a mean size greater than 900 $\mu$m, sieve analysis was used to determine particle size and particle size distribution.

Particle size and bulk density of each of the three quartz sediments were measured. The mean particle size was 19.0, 474.5 and 1250 $\mu$m for the fine-grained, fine+coarse mixture, and course-grained quartz sediments respectively. Particle size and distribution was constant with depth for each composite core. Bulk density was the only variable parameter in each core.

Bulk density was determined as a function of depth for the fine and coarse-grained quartz sediment at 30 cm core lengths and 20 cm core length for the fine+coarse mixture. Consolidation times were 2 days for the fine-grained and fine+coarse mixture cores and was 1 day for the coarse-grained quartz sediments. Densities were determined by measuring the water content of each core in 2.5 cm increments. The average bulk density for the fine grain quartz sediment was 1.8 g/cm$^3$. The fine+coarse quartz mixture had an average of 2.07 g/cm$^3$. The average bulk density for the coarse-grained quartz sediment was 1.925 g/cm$^3$.

Shear stresses of 0.5, 1.0, and 2.0 Pa were run for each of the three quartz sediments. For the coarse-grained quartz, the particles were observed to transport entirely as bedload and fell into the first trap for all shear stresses. For the mixture, it was observed that only the coarse fraction transported as bedload and fell into the first trap while the fine-grained fraction eroded into suspension. The fine-grained quartz sediment eroded into suspension for all shear stresses. The measured results for the bedload and suspended load are summarized in Tables 1, 2, and 3 for the fine-grained, coarse-grained, and fine+coarse mixture respectively. Column 7, "Total Mass Eroded (dry)" is calculated by using Eq. (4).

The data shows that for the fine-grained quartz, there was some material measured in each trap and at each shear stress. The amount was less than 1% for each trap. This material could have possibly been due to: (1) the small amount of quartz between 50 and 100 $\mu$m in size that was associated with the fine-grained quartz and traveled as bedload or (2)

the settling of grains that were suspended in the 2 liters of water that the traps hold. The first explanation could not be directly supported because there was not enough sample (<1 g) to particle size the amount in the traps and determine if the material was due to bedload. The second explanation is supported by the data from the suspended load measurements because the amount captured was very close to the amount that was suspended in the 2 liters of water in the traps. This was consistent for all traps and shear stresses.

By mass, over 99% of the measured material (bedload and suspended load combined) was in suspension. The total mass balance between that eroded and that captured as bedload and suspended load was between 83% and 114% and was determined almost entirely by the suspended load measurements.

The data for the coarse-grained quartz shows that all of the material transported as bedload and virtually all the material was captured in the first trap. The exception is for the 2.0 Pa test in which some of the material was captured in traps 2 and 3. Trap 2 captured only 1% of the total eroded material, and particle size analysis determined that it was made up of the finer fraction associated with the coarse-grained quartz (1250 $\mu$m mean size). The size distribution for the coarse-grained quartz shows that only 5% is less than 850 $\mu$m. The material captured in trap 2 during the 2.0 Pa test had 34% less than 850 $\mu$m. Trap 3 did not contain enough sample for particle size analysis.

By mass, 100% of the measured material (bedload and suspended load combined) was transported as bedload. The total mass balance between that eroded and that captured as bedload and suspended load was between 88% and 108% and was determined entirely by the bedload measurements.

The data for the mixed sample shows that bedload and suspended load were separated by the particle size of the material eroded. None of the coarse-grained material was transported in suspension and the amount of coarse material measured in the traps was essentially equal to the amount of coarse material (37% of total) eroded for each test. Likewise, the amount of material measured in suspension was within 80% of the fine grain fraction (63% of total) eroded.

The 1.0 Pa test was done without refilling the tank with clean water upon completion of the 0.5 Pa test. In addition, the re-used water was also allowed to set without flow for over 15 minutes. Much of the material from the 0.5 Pa test may have settled and was not accounted for in the measurement. Therefore, the data for the 1.0 Pa test is suspect and should be viewed as possibly being incorrect.

By means of the experiments described here, bedload and suspended load were measured as a function of shear stress for three quartz sediments. From these experiments, the following was determined for all shear stresses tested. (1) For the fine-grained quartz, virtually all of the material was in suspension and measured as such. (2) For the coarse-graineded quartz, essentially all of the material was observed and measured as bedload. (3) For the mixed quartz test, bedload and suspended load transport were separated by the size of the particles eroded.

The experiments demonstrate that the ASSET Flume is effective in capturing bedload accurately and can be combined with suspended load measurements to determine total transport. Mass balance shows experimental error of +/−17% for the suspended load measurements, +/−13% for the bedload measurement, and +/−15% when there is significant combined bedload and suspended load transport. Therefore, by means of the ASSET Flume, sediment transport characteristics can be quantitatively determined in conjunction with erosion characteristics.

The particular examples discussed above are cited to illustrate particular embodiments of the invention. Other applications and embodiments of the apparatus and method of the present invention will become evident to those skilled in the art.

The actual scope of the invention is defined by the claims appended hereto.

We claim:

1. An apparatus for eroding a sediment core sample and for trapping transported bedload sediments, comprising:
   channel means for conveying a flowing stream of liquid;
   erosion means, attached to a first opening in the bottom of the channel means, for exposing the sediment core sample to shear stresses applied by the flowing stream of liquid, whereby sediments are eroded and introduced into the flow stream; and
   trapping means, attached to a second opening in the bottom of the channel means at a location downstream from the first opening, for gravitationally separating transported bedload sediments from the flow stream and for capturing them.

2. The apparatus of claim 1, further comprising sampling means for sampling the flowing stream of liquid, whereby the suspended load concentration can be measured.

3. The apparatus of claim 1, wherein the channel means comprises a closed channel.

4. The apparatus of claim 3, wherein the closed channel comprises a rectangular cross-section having a width and a height.

5. The apparatus of claim 4, wherein the channel height is sufficiently tall to have a boundary layer that is at least 90% of free stream conditions.

6. The apparatus of claim 4, wherein the channel width is approximately 10 cm.

7. The apparatus of claim 4, wherein the channel height is greater than 2 cm.

8. The apparatus of claim 4, wherein the channel height is approximately 5 cm.

9. The apparatus of claim 4, wherein the rectangular channel comprises a water-tight assembly comprising a bottom plate, a top plate, and sidewalls.

10. The apparatus of claim 4, further comprising a flow converter attached to said rectangular channel for converting from a round cross section of pipe to the rectangular cross section of the channel.

11. The apparatus of claim 1, wherein the channel means is transparent.

12. The apparatus of claim 11, wherein the channel means comprises a clear plastic material.

13. The apparatus of claim 1, wherein the channel means is substantially straight, and is oriented substantially horizontal with respect to gravity.

14. The apparatus of claim 1, wherein the channel means is tilted about its longitudinal axis.

15. The apparatus of claim 1, mounted on a mobile platform capable of being moved to a test site in the field.

16. The apparatus of claim 1, further comprising means for forcing a flow of water in the channel means at a substantially constant velocity from 0.25 m/s to 2.5 m/s.

17. The apparatus of claim 1, further comprising means for forcing a flow of water in the channel means to create a shear stress greater than 10 N/m$^2$.

18. The apparatus of claim 1, wherein the liquid comprises water.

19. The apparatus of claim 1, further comprising pressure-regulating means attached to the top of the channel means, for allowing atmospheric pressure to be established inside the channel means.

20. The apparatus of claim 19, wherein said pressure-regulating means comprises a valve.

21. The apparatus of claim 20, wherein the valve is capable of receiving tubing capable of sampling a small volume of fluid from inside the channel means.

22. The apparatus of claim 21, further comprising a syringe attached to the end of the tubing, used for drawing up the small volume of fluid.

23. The apparatus of claim 1, further comprising means for establishing an elevated pressure above atmospheric pressure in the channel means.

24. The apparatus of claim 1, wherein said erosion means comprises a coring tube removeably attached to the first opening in the bottom of the channel means, for supporting the sediment core sample while being pushed into the flow stream.

25. The apparatus of claim 24, wherein the coring tube is cylindrical and has a diameter substantially equal to the width of the channel means.

26. The apparatus of claim 25, wherein the diameter of the coring tube is approximately 10 cm.

27. The apparatus of claim 24, wherein the coring tube has a rectangular cross section, and has a width substantially equal to the width of the channel means.

28. The apparatus of claim 27, wherein the coring tube has a width approximately equal to 10 cm, and a horizontal length approximately equal to 15 cm.

29. The apparatus of claim 24, wherein the coring tube has a vertical height approximately equal to 1 meter.

30. The apparatus of claim 24, wherein the coring tube is transparent.

31. The apparatus of claim 24, wherein the coring tube comprises means for extending its length by adding one or more extension tube segments.

32. The apparatus of claim 24, further comprising vertical drive means for pushing the sediment core sample into the flow stream.

33. The apparatus of claim 32, wherein the vertical drive means comprises piston means, disposed inside of the coring tube, for pushing the bottom of the sediment core sample; and further comprising a motorized jack drive mechanism for moving the piston means; and a displacement controller, operatively associated with the jack drive mechanism, for controlling the displacement of the sample.

34. The apparatus of claim 33, wherein the vertical drive means has a vertical position accuracy of +/−0.25 mm.

35. The apparatus of claim 1, further comprising means for measuring the length of the sediment core sample.

36. The apparatus of claim 1, wherein the sediment core sample is taken directly in the field.

37. The apparatus of claim 1, wherein the sediment core sample is prepared in a laboratory.

38. The apparatus of claim 1, wherein the trapping means comprises a capture basin.

39. The apparatus of claim 38, wherein said capture basin does not have any internal baffle structure.

40. The apparatus of claim 38, wherein said capture basin comprises means for creating a quiescent flow condition inside of the basin, to minimize interference with the hydrodynamics and velocity vectors of the main flow stream, and to increase the trapping efficiency by preventing fluid re-circulating zones from ejecting bedload sediments out of the trap and back into the main flow stream.

41. The apparatus of claim 38, wherein said means for creating a quiescent flow condition inside of the capture basin comprises an internal baffle structure disposed inside of the basin.

42. The apparatus of claim 41, wherein the internal baffle structure comprises: a plurality of angled baffles attached to the sidewalls of basin, which are angled downwards to permit particles to slide or roll down the angled baffles.

43. The apparatus of claim 41, wherein the internal baffle structure comprises a plurality of vertically oriented baffles.

44. The apparatus of claim 41, wherein the internal baffle structure comprises: two long, vertical baffles placed on either side of the centerline of the basin in the basin's upper half; one, long vertical baffle placed in the lower half of the basin along its centerline; and two, short vertical baffles placed on either side of the centerline in the lower half of the basin.

45. The apparatus of claim 44, wherein the internal baffle structure comprises a plurality of angled baffles placed at roughly a 45 degree angle within the basin; wherein all of the baffles are substantially parallel to each other, and are evenly spaced apart.

46. The apparatus of claim 41, wherein the internal baffle structure comprises a honeycomb structure.

47. The apparatus of claim 38, wherein the horizontal length of the capture basin is sufficiently long to capture substantially all of the transported eroded bedload sediments that flow past the capture basin.

48. The apparatus of claim 47, wherein the horizontal length of the capture basin is approximately 15 cm.

49. The apparatus of claim 38, wherein the width of the capture basin substantially matches the width of the channel means.

50. The method of claim 38, further comprising means for creating a quiescent flow condition inside the capture basin.

51. The method of claim 38, further comprising means for disrupting and inhibiting recirculation of fluid inside the capture basin.

52. The apparatus of claim 38, wherein the capture basin comprises a lower section comprising inwardly-tapered sidewalls, which serve to funnel the collected bedload particles into a collection region.

53. The apparatus of claim 52, further comprising valve means attached to an open lower end of the collection region for draining out the accumulated particles and overlying fluid.

54. The apparatus of claim 53, where the valve means comprises a 2" ball valve.

55. The apparatus of claim 1, wherein the trapping means comprises a plurality of traps disposed downstream of the erosion means.

56. The apparatus of claim 55, wherein the plurality of traps comprises three traps.

57. The apparatus of claim 56, wherein the first of the three traps is located approximately 1 meter downstream of the erosion means, and wherein each adjacent trap is spaced approximately 1 meter apart from one another.

58. The apparatus of claim 55, wherein any combination of traps can be closed or open during testing.

59. The apparatus of claim 1, wherein the length of the channel means upstream of the erosion means is sufficiently long so that fully-developed turbulent flow exists in the channel means at the location of the erosion means.

60. The apparatus of claim 59, wherein the length of the channel means upstream of the erosion means is greater than or equal to twenty-five times the hydraulic diameter of the channel means.

61. The apparatus of claim 59, wherein the length of said upstream length of straight channel is approximately 200 cm.

62. The apparatus of claim 1, further comprising:
   piping means, attached to the erosion means, for recirculating water through the apparatus of claim 1;

a storage tank, attached to the piping means, for storing and supplying water to the piping means; and pump means, attached to the piping means, for forcing the flow of water through the piping means.

63. The system of claim 62, further comprising a 3-way diverter valve connected to bypass piping, for bypassing the flow of water from the pump means back to the storage tank.

64. The system of claim 62, further comprising a means, operatively associated with the piping means, for measuring the flow rate of water in the system.

65. The system of claim 62, wherein the piping means comprises 2" diameter inlet and bypass piping, a downstream flow converter, and 3" diameter return piping.

66. A method of measuring an average total erosion rate from a sediment core sample, using the apparatus of claim 1, comprising:

flowing a stream of liquid in the channel;
exposing the sediment core sample to shear stresses applied by the flowing stream;
eroding sediments from the sample;
measuring the change in length of the sediment core sample over a known time interval;
calculating an average total erosion rate by dividing the measured length change by the known time interval, and
continuously maintaining the surface of the sediment core sample at a position that is level with the bottom surface of the channel during erosion of sediments from the core sample.

67. A method of measuring an average total erosion rate from a sediment core sample, using the apparatus of claim 1, comprising:

flowing a stream of liquid in the channel;
exposing the sediment core sample to shear stresses applied by the flowing stream;
eroding sediments from the sample;
measuring the change in length of the sediment core sample over a known time interval;
calculating an average total erosion rate by dividing the measured length change by the known time interval,
using a correction factor to correct for a channel height that has a boundary layer thickness less than 90% of the free stream condition; and
using a calibration curve of transport results generated using known quartz standards for the sample sediments.

68. The apparatus of claim 1, further comprising injection means for introducing a second stream of sediment particles into the flowing stream of liquid.

69. The apparatus of claim 68, wherein the injection means comprises a hopper containing a second source of sediment particles, the hopper attached to an opening in the upperside of the channel means.

70. The apparatus of claim 68, wherein the injection means comprises a holding tank comprising water and the second source of sediment particles; mixing means for mixing the water and the second source of sediment particles to form a mixture, and valve means attached to the bottom of the holding tank for controlling the flow by gravity of the mixture into an opening in the upperside of the channel means.

71. The apparatus of claim 1, further comprising two or more erosion means, each attached to an opening in the bottom of the channel means, and disposed in a serial fashion along the length of the channel means, for exposing two or more sediment core samples to shear stresses applied by the same flowing stream of liquid, whereby sediments are eroded from two or more sediment core samples and simultaneously introduced into the flow stream at two or more locations.

72. A method of eroding a sediment core sample and trapping transported bedload sediments, comprising:

a) flowing a stream of liquid in a channel;
b) exposing the sediment core sample to shear stresses applied by the flowing stream of liquid;
c) eroding sediments and introducing them into the flow stream; and
d) gravitationally separating transported bedload sediments from the flow stream and capturing them.

73. The method of claim 72, further comprising introducing a second stream of sediment particles into the flowing stream of liquid.

74. The method of claim 73, wherein introducing a second stream of sediment particles comprises adding said second source of sediment particles through an opening in the upperside of the channel.

75. The method of claim 72, further comprising eroding sediments from two or more locations disposed serially along the length of the channel.

76. The method of claim 72, further comprising continuously maintaining the surface of the sediment core sample at a position that is level with the bottom surface of the channel during erosion testing.

77. The method of claim 72, further comprising exposing a part of the channel to atmospheric pressure to prevent development of negative pressures inside the channel.

78. The method of claim 72, further comprising operating the apparatus of claim 46 with only one of the plurality of traps being open to collect sediments during erosion testing, the other traps being closed.

79. The method of claim 78, further comprising:

a) taking a first measurement of the transported bedload sediments with only a first trap being open to capture particles;
b) taking a second measurement of the transported bedload sediments with only a second trap being open to capture particles;
c) taking a third measurement of the transported bedload sediments with only a third trap being open to capture particles; and
d) using the first, second, and third measurements to understand the disaggregation of cohesive particles as a function of transport down the channel means.

80. A method of measuring a bedload sediment erosion rate from a sediment core sample, comprising:

a) flowing a stream of liquid in the channel;
b) exposing the sediment core sample to shear stresses applied by the flowing stream;
c) eroding sediments and introducing them into the flow stream;
d) transporting the bedload sediments downstream;
e) gravitationally separating the transported bedload sediments from the flow stream and capturing them;
f) measuring the amount of transported bedload sediments captured in step e) during a known interval of time; and
g) calculating the bedload sediment erosion rate, by dividing the amount measured in step f) by the known interval of time.

81. The method of claim 80, further comprising using the apparatus of claim 1 to perform steps a) through e).

\* \* \* \* \*